US008003386B1

(12) United States Patent
Gentz et al.

(10) Patent No.: US 8,003,386 B1
(45) Date of Patent: Aug. 23, 2011

(54) TUMOR NECROSIS FACTOR RECEPTORS 6α AND 6β

(75) Inventors: Reiner Gentz, Silver Spring, MD (US);
Reinhard Ebner, Gaithersburg, MD (US); Guo-Liang Yu, Darnestown, MD (US); Steven M. Ruben, Olney, MD (US); Jian Ni, Rockville, MD (US); Ping Feng, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 3305 days.

(21) Appl. No.: 09/006,352

(22) Filed: Jan. 13, 1998

Related U.S. Application Data

(60) Provisional application No. 60/035,496, filed on Jan. 14, 1997.

(51) Int. Cl.
*C12N 15/28* (2006.01)
*C12N 15/09* (2006.01)
*C12N 15/06* (2006.01)
*C12N 15/12* (2006.01)
*C12N 5/10* (2006.01)
*C12P 21/00* (2006.01)

(52) U.S. Cl. ....... 435/361; 435/69.1; 435/325; 530/350; 536/23.5

(58) Field of Classification Search .......... 530/350; 536/23.5; 435/320.1, 252.3, 325, 69.1
See application file for complete search history.

(56) References Cited

U.S. PATENT DOCUMENTS

| | | | |
|---|---|---|---|
| 5,620,889 A | 4/1997 | Lynch et al. | |
| 5,632,994 A | 5/1997 | Reed et al. | |
| 5,652,210 A | 7/1997 | Barr et al. | |
| 5,663,070 A | 9/1997 | Barr et al. | |
| 5,741,667 A | 4/1998 | Goeddel et al. | |
| 5,830,469 A | 11/1998 | Lynch et al. | |
| 5,874,546 A | 2/1999 | Nagata et al. | |
| 5,885,800 A * | 3/1999 | Emery et al. | 435/69.1 |
| 6,297,367 B1 | 10/2001 | Tribouley | |

FOREIGN PATENT DOCUMENTS

| | | |
|---|---|---|
| EP | 0 861 850 | 9/1998 |
| WO | WO95/33051 | 12/1995 |
| WO | WO96/34095 | 10/1996 |
| WO | WO98/56892 | 12/1998 |
| WO | WO99/04001 | 1/1999 |
| WO | WO99/07738 | 2/1999 |
| WO | WO99/11791 | 3/1999 |
| WO | WO99/14330 | 3/1999 |
| WO | WO99/26977 | 6/1999 |
| WO | WO99/31128 | 6/1999 |
| WO | WO99/33980 | 7/1999 |
| WO | WO99/46376 | 9/1999 |
| WO | WO99/50413 | 10/1999 |
| WO | WO00/01817 | 1/2000 |

OTHER PUBLICATIONS

Skolnick et al., From genes to protein structure and function: novel applications of computational approaches in the genomic era. Trends in Biotechnology, pp. 34-39, 2000.*
Yan et al. Two-Amino Acid Molecular Switch in an Epithelial Morphogen That Regulates Binding to Two Distinct Receptors. Science, Vo. 290, Oct. 20, 2000, pp. 523-527.*
EMBL Database Accession No. AA025673 Aug. 16, 1996.
Kwon et al., The J. of Biol. Chem., 272:14272-14276 (1997).
EMBL Database Accession No. W67560 (Oct. 16, 1996).
EMBL Database Accession No. M91489 (Oct. 29, 1992).
Gieser and Swaroop, Genomics 13(3):873-876 (Jul. 1992).
Hillier et al., Genome Research 6:807-828 (1996).
Pitti et al., Nature, 396:699-703 (Dec. 17, 1998).
Rabinowich et al., "Lymphocyte Apoptosis Induced by Fas Ligand-expressing Ovarian Carcinoma Cells," J. Clin. Invest. 101(11):2579-2588 (Jun. 1998).
Walker et al., "Tumor expression of Fas ligand (CD95L) and the consequences," Current Opinion in Immunology 10:564-572 (1998).
Gratas, et al., "Up-Regulation of Fas (APO-1/CD95) Ligand and Down-Regulation of Fas Expression in Human Esophageal Cancer," Cancer Research 58:2057-2062 (May 15, 1998).
Adams et al., Initial assessment of human gene diversity and expression patterns based upon 83 million nucleotides of cDNA sequence. Nature 377 (6547 Suppl):3-174 (1995).
Adams et al., Genbank Accession No. AA325843 (Apr. 20, 1997).
Hillier et al., Genbank Accession No. AA025672 (Feb. 1, 1997).
Zhang et al., Modulation of T-cell responses to alloantigens by TR6/DcR3. J. Clin Invest. 107:1459-1468.
U.S. Appl. No. 09/912,293, Rosen et al.

* cited by examiner

*Primary Examiner* — Christine J Saoud
*Assistant Examiner* — Jon M Lockard

(57) ABSTRACT

The present invention relates to novel Tumor Necorsis Factor Receptor proteins. In particular, isolated nucleic acid molecules are provided encoding the human TNFR-6α & -6β proteins. TNFR-6α & -6β polypeptides are also provided as are vectors, host cells and recombinant methods for producing the same. The invention further relates to screening methods for identifying agonists and antagonists of TNFR-6α & -6β activity. Also provided are diagnostic methods for detecting immune system-related disorders and therapeutic methods for treating immune system-related disorders.

104 Claims, 22 Drawing Sheets

```
GCTCTCCCTGCTCCAGCAAGGACCATGAGGGCGCTGGAGGGGCCAGGCCTGTCGCTGCTG
                       M  R  A  L  E  G  P  G  L  S  L  L

TGCCTGGTGTTGGCGCTGCCTGCCCTGCTGCCGGTGCCGGCTGTACGCGGAGTGGCAGAA
 C  L  V  L  A  L  P  A  L  L  P  V  P  A  V  R  G  V  A  E

ACACCCACCTACCCCTGGCGGGACGCAGAGACAGGGGAGCGGCTGGTGTGCGCCCAGTGC
 T  P  T  Y  P  W  R  D  A  E  T  G  E  R  L  V  C  A  Q  C

CCCCCAGGCACCTTTGTGCAGCGGCCGTGCCGCCGAGACAGCCCCACGACGTGTGGCCCG
 P  P  G  T  F  V  Q  R  P  C  R  R  D  S  P  T  T  C  G  P

TGTCCACCGCGCCACTACACGCAGTTCTGGAACTACCTGGAGCGCTGCCGCTACTGCAAC
 C  P  P  R  H  Y  T  Q  F  W  N  Y  L  E  R  C  R  Y  C  N

GTCCTCTGCGGGGAGCGTGAGGAGGAGGCACGGGCTTGCCACGCCACCCACAACCGTGCC
 V  L  C  G  E  R  E  E  E  A  R  A  C  H  A  T  H  N  R  A

TGCCGCTGCCGCACCGGCTTCTTCGCGCACGCTGGTTTCTGCTTGGAGCACGCATCGTGT
 C  R  C  R  T  G  F  F  A  H  A  G  F  C  L  E  H  A  S  C

CCACCTGGTGCCGGCGTGATTGCCCCGGGCACCCCCAGCCAGAACACGCAGTGCCAGCCG
 P  P  G  A  G  V  I  A  P  G  T  P  S  Q  N  T  Q  C  Q  P

TGCCCCCCAGGCACCTTCTCAGCCAGCAGCTCCAGCTCAGAGCAGTGCCAGCCCCACCGC
 C  P  P  G  T  F  S  A  S  S  S  S  S  E  Q  C  Q  P  H  R

AACTGCACGGCCCTGGGCCTGGCCCTCAATGTGCCAGGCTCTTCCTCCCATGACACCCTG
 N  C  T  A  L  G  L  A  L  N  V  P  G  S  S  S  H  D  T  L

TGCACCAGCTGCACTGGCTTCCCCCTCAGCACCAGGGTACCAGGAGCTGAGGAGTGTGAG
 C  T  S  C  T  G  F  P  L  S  T  R  V  P  G  A  E  E  C  E

CGTGCCGTCATCGACTTTGTGGCTTTCCAGGACATCTCCATCAAGAGGCTGCAGCGGCTG
 R  A  V  I  D  F  V  A  F  Q  D  I  S  I  K  R  L  Q  R  L

CTGCAGGCCCTCGAGGCCCCGGAGGGCTGGGCTCCGACACCAAGGGCGGGCCGCGCGGCC
 L  Q  A  L  E  A  P  E  G  W  G  P  T  P  R  A  G  R  A  A

TTGCAGCTGAAGCTGCGTCGGCGGCTCACGGAGCTCCTGGGGGCGCAGGACGGGGCGCTG
 L  Q  L  K  L  R  R  R  L  T  E  L  L  G  A  Q  D  G  A  L

CTGGTGCGGCTGCTGCAGGCGCTGCGCGTGGCCAGGATGCCCGGGCTGGAGCGGAGCGTC
 L  V  R  L  L  Q  A  L  R  V  A  R  M  P  G  L  E  R  S  V

CGTGAGCGCTTCCTCCCTGTGCACTGATCCTGGCCCCCTCTTATTTATTCTACATCCTTG
 R  E  R  F  L  P  V  H  *

GCACCCCACTTGCACTGAAAGAGGCTTTTTTTTTAAATAGAAGAAATGAGGTTTCTTAAAG

CTTATTTTTTATAAAGCTTTTTCATAAAAAAAAAAAAAAAAAAAAAAAAAAAAAAAAAA
```

FIG. 1

TGGCATGTCGGTCAGGCACAGCAGGGTCCTGTGTCCGCGCTGAGCCGCGCTCTCCCTGCT

CCAGCAAGGACCATGAGGGCGCTGGAGGGGCCAGGCCTGTCGCTGCTGTGCCTGGTGTTG
           M  R  A  L  E  G  P  G  L  S  L  L  C  L  V  L

GCGCTGCCTGCCCTGCTGCCGGTGCCGGCTGTACGCGGAGTGGCAGAAACACCCACCTAC
A  L  P  A  L  L  P  V  P  A  V  R  G  V  A  E  T  P  T  Y

CCCTGGCGGGACGCAGAGACAGGGGAGCGGCTGGTGTGCGCCCAGTGCCCCCCAGGCACC
P  W  R  D  A  E  T  G  E  R  L  V  C  A  Q  C  P  P  G  T

TTTGTGCAGCGGCCGTGCCGCCGAGACAGCCCCACGACGTGTGGCCCGTGTCCACCGCGC
F  V  Q  R  P  C  R  R  D  S  P  T  T  C  G  P  C  P  P  R

CACTACACGCAGTTCTGGAACTACCTGGAGCGCTGCCGCTACTGCAACGTCCTCTGCGGG
H  Y  T  Q  F  W  N  Y  L  E  R  C  R  Y  C  N  V  L  C  G

GAGCGTGAGGAGGAGGCACGGGCTTGCCACGCCACCCACAACCGTGCCTGCCGCTGCCGC
E  R  E  E  E  A  R  A  C  H  A  T  H  N  R  A  C  R  C  R

ACCGGCTTCTTCGCGCACGCTGGTTTCTGCTTGGAGCACGCATCGTGTCCACCTGGTGCC
T  G  F  F  A  H  A  G  F  C  L  E  H  A  S  C  P  P  G  A

GGCGTGATTGCCCCGGGTGAGAGCTGGGCGAGGGGAGGGGCCCCCAGGAGTGGTGGCCGG
G  V  I  A  P  G  E  S  W  A  R  G  G  A  P  R  S  G  G  R

AGGTGTGGCAGGGGTCAGGTTGCTGGTCCCAGCCTTGCACCCTGAGCTAGGACACCAGTT
R  C  G  R  G  Q  V  A  G  P  S  L  A  P  *

CCCCTGACCCTGTTCTTCCCTCCTGGCTGCAGGCACCCCCAGCCAGAACACGCAGTGCCA

GCCGTGCCCCCCAGGCACCTTCTCAGCCAGCAGCTCCAGCTCAGAGCAGTGCCAGCCCCA

CCGCAACTGCACGGCCCTGGGCCTGGCCCTCAATGTGCCAGGCTCTTCCTCCCATGACAC

CCTGTGCACCAGCTGCACTGGCTTCCCCCTCAGCACCAGGGTACCAGGTGAGCCAGAGGC

CTGAGGGGGCAGCACACTGCAGGCCAGGCCCACTTGTGCCCTCACTCCTGCCCCTGCACG

TGCATCTAGCCTGAGGCATGCCAGCTGGCTCTGGGAAGGGGCCACAGTGGATTTGAGGGG

TCAGGGGTCCCTCCACTAGATCCCCACCAAGTCTGCCCTCTCAGGGGTGGCTGAGAATTT

GGATCTGAGCCAGGGCACAGCCTCCCCTGGAGAGCTCTGGGAAAGTGGGCAGCAATCTCC

FIG.2A

```
TAACTGCCCGAGGGGAAGGTGGCTGGCTCCTCTGACACGGGGAAACCGAGGCCTGATGGT

AACTCTCCTAACTGCCTGAGAGGAAGGTGGCTGCCTCCTCTGACATGGGGAAACCGAGGC

CCAATGTTAACCACTGTTGAGAAGTCACAGGGGGAAGTGACCCCCTTAACATCAAGTCAG

GTCCGGTCCATCTGCAGGTCCCAACTCGCCCCTTCCGATGGCCCAGGAGCCCCAAGCCCT

TGCCTGGGCCCCCTTGCCTCTTGCAGCCAAGGTCCGAGTGGCCGCTCCTGCCCCCTAGGC

CTTTGCTCCAGCTCTCTGACCGAAGGCTCCTGCCCCTTCTCCAGTCCCCATCGTTGCACT

GCCCTCTCCAGCACGGCTCACTGCACAGGGATTTCTCTCTCCTGCAAACCCCCCGAGTGG

GGCCCAGAAAGCAGGGTACCTGGCAGCCCCCGCCAGTGTGTGTGGGTGAAATGATCGGAC

CGCTGCCTCCCCACCCCACTGCAGGAGCTGAGGAGTGTGAGCGTGCCGTCATCGACTTTG

TGGCTTTCCAGGACATCTCCATCAAGAGGAGCGGCTGCTGCAGGCCC
```

| | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| 198 | - | G | A | V | H | L | P | Q | P | - | - | - | - | - | - | - | - | - | - | - | - | - | - | - | - | - | - | - | - | - | - | - | - | - | - | - | TNFR1 |

(Figure content — multiple sequence alignment)

FIG.3G

```
223  - - - - - - - - - - - - - - - - - - - - C L L S L L F I G L M Y - - - - - - - - - - TNFR1
252  L G S T G D F A L - - - - - - - - - - - - P V G L T V G V T A L G L L I G V V - - TNFR2
236  M G S S Q P V V T R G T T D N L I P V Y C S I L A A V V G L V A - - - - - - - - - NGFR
230  - - - - - - L - - - - - - - - - - - - - - V L F L L F T T V L A C A W M R H P S LTbR
178  - - - - - - - - - - - - - - - - - - - - - C L L - L L P I P L I V - - - - - - - - FAS
164  - A D - - - - - - - - - - - - - - - - - - - - - - - - - - - - - - - - - - - - - - CD27
242  K Q C E P D Y Y L D E A G R C T A C V S C S R D D L V E K T P C A W N S S R T C - CD30
200  - - - - - - - - - - - - - - - - - - - - - I F G I L F A I L L V L V F I K K - - - CD40
190  - - - - - F F L - - - - - - - - - - - - - - - - - - - - - - - - - - - - - - - - - 4-1BB
184  - - A R P I T V Q P T E A - - - - - - - - - - - - - - - - - - - - - - - - - - - - OX40
221  P V F R E E Y - - - - - - - - - - - - - - F S V L N K V A T S G F F T G E N R - - VC22
221  P V F R N G Y - - - - - - - - - - - - - - F S V L N E V A T S G F F T G Q N R - - CRMB

208  A E E C E R - - - - - - - - - - - - - - - - - - - - - - - - - - - A V I - - - - - TNFR-6a
143  - - - - - - - - - - - - - - - - - - - - - - - - - - - - - - - - - - - - - - - - - TNFR-6b
```

FIG.3H

```
235 - - R Y Q R W - S K L Y S I - - - - - - - V C G K S T P E K E G E L L E G T T  TNFR1
280 N C V - - I M T Q V K K P L C - - - - - - - - - - - - - - - - - - - - - - - -  TNFR2
269 - - - - - Y I A F K R W N S C K Q - - - - - - - - - - - - - - - - - - - - - -  NGFR
250 L C R - - K L G T L L R H - - - - - - - - - - - - - - - - - - - - - - - - - -  LTbR
189 - - - - - - - - W V R K E V Q K - - - - - - - - - - - - - - - - - - - - - - -  FAS
166 - - - - - - - - - F R Q - - - - - - - - T C R K H R K E N Q G S H E - - - - -  CD27
282 E C R P G M I C A T S A T N S C A R C V P Y P I C A A E T V T K P Q D M A E K D  CD30
218 - - - - - - - - V A K K - - - - - - - - - - - - - - - - - - - - - - - - - - -  CD40
193 - - - - - - - - - - - - - - - - - - - - - - - - - - - - - - - - - - - - - - -  4-1BB
195 - - - - - - - W P - - R - - - - - - - - - - - - - - - - - - - - - - - - - - -  OX40
246 - - - - - Y Q N I S - K - - V C T - - - - - - - - - - - - - - - - - - - - - -  VC22
246 - - - - - Y Q N I S - K - - V C T - - - - - - - - - - - - - - - - - - - - - -  CRMB

217 D F V - - A F Q D I S I K R - - - - - - - - - - - - - - - - - - - - - - - - -  TNFR-6a
143 - - - - - - - - - - - - - - - - - - - - - - - - - - - - - - - - - - - - - - -  TNFR-6b
```

```
304  C P N F A A P R R E V A P P Y Q G A D P I L A T A - - - - - - - -   TNFR1
324  - - - - - P S S S S S S L E S S A S A L - - - - - - - - - - - - -   TNFR2
311  S Q S L H D Q Q P H T Q T A S G Q A L K - - - - - - - - - - - - -   NGFR
288  - - - - - P M S G D L S P S P A G P P T - G D G G L Y S S L P P A K R E E   LTbR
236  - - - - - - - - - - - - - - - - - U A G V - - - - - - - - - - - -   FAS
171  A R T L S T H W P P Q R S L C S S D F I - - R I L V I F S G M F L V F T L A   CD27
361  S K T L P I P T S A P V A L S - T G K P V L D A G P V L F W V I L V L V V V G   CD30
241  - - - - - - - - - D L P G - N I A P V - - - - - - - - - - - - - V   CD40
193  - - - - - - - - - - - - - A L I S T A L L F L - L F F L T L R F S V V K R   4-1BB
224  - - - - - - - - - - - - - - - - V L G L L - - G P L A I L L A L Y L L R R D Q   OX40
274  - - - - - A K N D D G - M - - - - - - - - - - - - - - - - - - - -   VC22
276  - - - - - T K N D D D D S I - - - - - - - - - - - - - - - - - - -   CRMB

FIG. 3G

246  - - - - - P R A G R A A L Q L K - - - L - - - - - - - - - - - -   TNFR-6a
151  - - - - - P R S G - - - - - - - - - - - - - - - - - - - - - - -   TNFR-6b

FIG. 3K
```

| | | | | | | | | | | | | | | | | | | | | | | | | | | |
|---|---|---|---|---|---|---|---|---|---|---|---|---|---|---|---|---|---|---|---|---|---|---|---|---|---|---|
| 329 | - | - | - | - | L | A | S | D | P | I | P | N | P | L | Q | K | W | E | D | S | A | H | K | P | Q | S | L | D | T | D | D | P | A | T | L | Y | A | V | V | E | TNFR1 |
| 339 | - | - | - | - | - | - | - | - | D | R | R | R | A | P | T | R | N | Q | P | Q | A | P | G | V | E | A | S | G | A | G | E | A | R | A | S | T | G | S | S | D | S | S | TNFR2 |
| 347 | V | E | K | L | L | - | - | - | - | - | - | - | - | - | - | - | - | - | - | - | - | - | - | - | - | - | - | - | - | - | - | - | - | - | N | G | S | NGFR |
| 303 | - | - | - | - | - | - | - | A | P | S | L | E | E | V | V | L | Q | Q | Q | S | P | L | - | - | - | - | - | - | - | - | - | - | - | - | V | Q | A | R | E | L | - | - | E | A | E | LTbR |
| 240 | - | - | - | - | M | T | L | S | Q | V | - | - | - | - | - | - | - | - | - | - | - | - | - | - | - | - | - | - | - | - | - | - | - | - | - | FAS |
| 207 | G | A | L | F | L | - | - | - | - | - | - | - | - | - | - | - | - | - | - | - | - | - | - | - | - | - | - | - | - | - | - | - | - | - | - | H | Q | - | CD27 |
| 401 | S | S | A | F | L | L | C | H | R | R | A | C | R | K | R | I | R | Q | K | L | H | L | C | Y | P | V | Q | T | S | Q | P | K | L | E | L | V | D | S | R | P | CD30 |
| 252 | - | - | - | - | - | Q | E | T | L | - | - | - | - | - | - | - | - | - | - | - | - | - | - | - | - | - | - | - | - | - | CD40 |
| 216 | G | R | K | K | L | L | - | - | - | - | - | - | - | - | - | - | - | - | - | - | - | - | - | - | - | - | - | - | - | - | - | - | - | - | 4-1BB |
| 245 | - | - | - | - | - | - | - | - | - | - | - | - | - | - | - | - | - | - | - | - | - | - | - | - | - | - | - | - | - | - | OX40 |
| 281 | - | - | - | - | - | - | - | - | - | - | - | M | S | H | S | E | T | V | T | L | A | G | D | C | L | S | S | V | D | I | Y | I | L | Y | S | N | T | N | VC22 |
| 284 | - | - | - | - | - | - | - | - | - | - | - | M | P | H | S | E | S | V | T | L | V | G | D | C | L | S | S | V | D | I | Y | I | L | Y | S | N | T | N | CRMB |
| 258 | - | - | - | - | - | - | - | - | - | - | - | R | R | R | L | T | E | L | L | G | A | Q | D | G | A | L | L | V | R | L | L | Q | A | L | R | - | TNFR-6a |
| 155 | - | - | - | - | - | - | - | - | - | - | - | - | - | - | - | - | - | - | - | - | - | - | - | - | - | - | - | - | - | - | - | - | - | - | - | TNFR-6b |

```
405 ATWRRRTPRREATLELLGRVLRDMDLLGC  -  -   -   -   -   -  - TNFR1
409  -  - DSSPSES-PKDE -  -  - QVPFSKEECAF  -  -   -   -   -  - TNFR2
388 ASWATQDSATLDA -  -   -   -   -   -   -   -   -   -   -   -   -  - NGFR
365  -  - RGPGDP-PAPP -  -  - EPPYPTPEEGA  -  -   -   -   -  - LTbR
279 RNWHQLHGKKEA-YDTLIKDLKKANL -  - CTLAEKIQ -   -   -   -  - FAS
239  -  - EEGSTI -  -   -   -   -   -   -   -   -   -   -   -   -  - CD27
481 ESLPLQDASPAGG-PSSPRDLPEPRVSTEHTNNKIEKIY -   -   -  - CD30
263  -  - SP -  -   -   -   -   -   -   -   -   -   -   -   -   -  - CD40
222  -   -   -   -   -   -   -   -   -   -   -   -  Y  - 4-1BB
260  -   -   -   -   -   -  PITNSK -   -   -   -   -   -   -  - OX40
339  -   -   -   -   -   -  LITNSNSQY -   -   -   -   -   -  - VC22
342  -   -   -   -   -   -   -   -   -   -   -   -   -   -   -  - CRMB

291  -   -   -   -   -   -   -   -   -   -   -   -   -   -   -  - TNFR-6a
163  -   -   -   -   -   -   -   -   -   -   -   -   -   -   -  - TNFR-6b
```

FIG.3N

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| 434 | - | - | - | - | - | L | E | D | I | E | E | A | L | C | G | P | A | A | L | P | - | - | - | - | - | - | - | - | - | - | - | - | TNFR1 |
| 431 | - | - | - | - | - | - | - | - | - | - | - | - | - | - | - | - | - | - | - | - | R | S | Q | L | E | T | P | E | T | L | L | G | S | T | E | E | K | TNFR2 |
| 401 | - | - | - | - | - | - | - | - | - | - | - | - | - | - | - | - | - | - | - | - | - | - | L | L | A | A | L | R | R | I | Q | R | A | D | NGFR |
| 386 | - | - | - | - | - | - | - | - | - | - | - | - | - | - | - | - | - | - | - | - | P | G | P | S | E | L | S | T | P | Y | Q | E | D | G | K | A | W | LTbR |
| 312 | - | - | - | - | T | I | I | L | K | D | I | T | S | D | - | S | E | N | S | N | F | R | - | - | - | - | - | - | - | - | - | - | - | FAS |
| 246 | - | - | - | - | - | - | - | - | - | - | - | - | - | - | - | - | - | - | - | - | - | - | - | - | - | - | - | - | - | - | - | - | P | CD27 |
| 520 | M | K | A | D | I | V | I | V | G | T | V | K | A | E | L | P | E | G | R | G | L | A | G | P | A | E | P | E | L | E | E | L | E | A | D | H | T | P | H | CD30 |
| 263 | - | - | - | - | - | - | - | - | - | - | - | - | - | - | - | - | - | - | - | - | - | - | - | - | - | - | - | - | - | - | - | Q | E | D | G | K | E | S | CD40 |
| 224 | - | F | K | - | - | - | - | - | - | - | - | - | - | - | - | - | - | - | - | - | - | - | - | - | - | - | - | Q | P | F | M | R | P | 4-1BB |
| 260 | - | - | - | - | - | - | - | - | - | - | - | - | - | - | - | - | - | - | - | - | - | - | - | - | - | - | - | - | - | - | - | - | V | Q | I | T | OX40 |
| 345 | - | - | - | - | - | - | - | - | - | - | - | - | - | - | - | - | - | - | - | - | P | T | R | F | - | - | - | - | - | - | - | - | R | T | P | VC22 |
| 351 | - | - | - | - | - | - | - | - | - | - | - | - | - | - | - | - | - | - | - | - | P | T | H | F | - | - | - | - | - | - | - | - | - | CRMB |
| 291 | - | - | - | - | - | - | - | - | - | - | - | - | - | - | - | - | - | - | - | - | - | - | - | - | - | - | - | - | - | - | - | - | S | V | R | E | R | TNFR-6a |
| 163 | - | - | - | - | - | - | - | - | - | - | - | - | - | - | - | - | - | - | - | - | - | - | - | - | - | - | - | - | - | - | - | - | V | A | G | P | S | TNFR-6b |

FIG. 30

```
449  - P - - - - - - - - - - - - - - - - - - L P L G V P D A G M K P S - P A P S L L R   TNFR1
448                                                                                      TNFR2
413  L V E S L C S E S - - - - - - - - - - - - - - - - - - - - - - -                     NGFR
403  H - - - - - - - - - - - - L A E T - E T L G C Q D L - - T A T S P V                 LTbR
329  - - - - - - - - - - - - - - - - - - - - - - - - - - N E I Q S L V                   FAS
247  I Q E D - Y R K P - - - - - - - - - - - - - - - - - E P A C S P                     CD27
560  Y P E Q E T E P P L G S C S D V M L S V E E G K E D P L P T A A S G K               CD30
270  R - - - - - - - - - - - - I S V Q - E R Q - - - - - - - - - - -                     CD40
236  Q E E D G C - - - - - - - - - R F P E E G - - - - - - - - - -                       4-1BB
263  I Q E Q - - - - - - - - - - - - - - - - - - - - - G C E L - -                       OX40
349  - - - - - - - - - - - - - - - - - - - - - L - - - - - S T L A K I                   VC22
355  - - - - - - - - - - - - - - - - - - - - - L - - - - - - - - -                       CRMB

296  F - - - - - - - - - - - - L P V - - - - - - H                                       TNFR-6a
168  L - - - - - - - - - - - - A P - - - - - - - -                                       TNFR-6b
```

FIG. 3P

HELDI06R
GGCACGAGCA GGGTCCTGTN TCCGCCCTGA GCCGCGCTCT NCCTGCTCCA GCAAGGACCA
TGAGGGCGCT GGAGGGGCCA GGCCTGTCGC TGCTGTGCCT GGTGTTGGCG CTGCCTGCCC
TGCTGCCGGT GCCGGCTGTA CGCGGAGTGG CAGAAACACN NACNTACCCC TGGCGGGACG
NAGAGACAGG GGAGCGGCTG GTGTNTNCCC ANTGCCCCCC AGGCACCTTT NTGCAGCGGC
CGTGCCGNCG AGACAGCCCC ACGACGTGTG GCCCGTNTCC ACCGCGCCAC TACACGCATT
CTGGAACTAC CTGGAGCGCT GNCGTTACTN CAACGTCCTC TGCGGGGAGC GTNAGGAGGA
GGCACGGGTT TNCCACGNCA ACCACAACCG NGGNTTACCG TNGCCGNACC GGTTTCTTCG
NGGCAAGTTG GTTTTTNNTT TGGAGNAAGG ATTCGTGTTN CAATTNATTG ACGNAGTGAT
TNNNCNCGGG AAACTNAAA

HCEOW38R
CGCAACTGCA CGGCCCTGGG ACTGGCCCTC AATGTGCCAG GNTCTTCCTC CCATGACACC
CTGTGCACCA GCTGCACTGG CTTCCCCCTC AGCACCAGGG TACCANGAGC TGAGGAGTGT
GAGCNTGCCG TCATCGACTT TTTGGCTTTC CAGGACATCT CCATCAAGAG GCTGCAGCGG
CTGCTCANGC C

FIG.6

TUMOR NECROSIS FACTOR RECEPTORS 6α AND 6β

This application claims benefit of 35 U.S.C. section 119(e) based on copending U.S. Provisional Application Ser. No. 60/035,496, filed Jan. 14, 1997, which is hereby incorporated herein by reference.

FIELD OF THE INVENTION

The present invention relates to novel human genes encoding polypeptides which are members of the TNF receptor family. More specifically, isolated nucleic acid molecules are provided encoding human polypeptides named tumor necrosis factor receptor-6α & -6β hereinafter sometimes referred to as "TNFR-6α, & -6β" or generically as "TNFR polypeptides". TNFR polypeptides are also provided, as are vectors, host cells and recombinant methods for producing the same. The invention further relates to screening methods for identifying agonists and antagonists of TNFR polypeptide activity. Also provided are diagnostic and therapeutic methods utilizing such compositions.

BACKGROUND OF THE INVENTION

Many biological actions, for instance, response to certain stimuli and natural biological processes, are controlled by factors, such as cytokines. Many cytokines act through receptors by engaging the receptor and producing an intra-cellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-α, lymphotoxin-α (LT-α, also known as TNF-β), LT-β (found in complex heterotrimer LT-α2-β), FasL, CD40L, CD27L, CD30L, 4-1BBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al., Cell 69:737 (1992)).

TNF and LT-α are capable of binding to two TNF receptors (the 55- and 75-kd TNF receptors). A large number of biological effects elicited by TNF and LT-α, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-α are involved in the pathogenesis of a wide range of diseases, including endotoxic shock, cerebral malaria, tumors, autoimmune disease, AIDS and graft-host rejection (Beutler, B. and Von Huffel, C., Science 264:667-668 (1994)). Mutations in the p55 Receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., Cell 74:845 (1993)).

Apoptosis, or programmed cell death, is a physiologic process essential to the normal development and homeostasis of multicellular organisms (H. Steller, Science 267, 1445-1449 (1995)). Derangements of apoptosis contribute to the pathogenesis of several human diseases including cancer, neurodegenerative disorders, and acquired immune deficiency syndrome (C. B. Thompson, Science 267, 1456-1462 (1995)). Recently, much attention has focused on the signal transduction and biological function of two cell surface death receptors, Fas/APO-1 and TNFR-1 (J. L. Cleveland, J. N. Ihle, Cell 81, 479-482 (1995); A. Fraser, G. Evan, Cell 85, 781-784 (1996); S. Nagata, P. Golstein, Science 267, 1449-56 (1995)). Both are members of the TNF receptor family which also include TNFR-2, low affinity NGFR, CD40, and CD30, among others (C. A. Smith, et al., Science 248, 1019-23 (1990); M. Tewari, V. M. Dixit, in Modular Texts in Molecular and Cell Biology M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain", which is distantly related to the *Drosophila* suicide gene, reaper (P. Golstein, D. Marguet, V. Depraetere, Cell 81, 185-6 (1995); K. White et al., Science 264, 677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (A. M. Chinnaiyan, K. O'Rourke, M. Tewari, V. M. Dixit, Cell 81, 505-12 (1995); M. P. Boldin, et al., J. Biol Chem 270, 7795-8 (1995); F. C. Kischkel, et al., EMBO 14, 5579-5588 (1995)), which in turn binds and presumably activates FLICE/MACH1, a member of the ICE/CED-3 family of pro-apoptotic proteases (M. Muzio et al., Cell 85, 817-827 (1996); M. P. Boldin, T. M. Goncharov, Y. V. Goltsev, D. Wallach, Cell 85, 803-815 (1996)). While the central role of Fas/APO-1 is to trigger cell death, TNFR-1 can signal an array of diverse biological activities-many of which stem from its ability to activate NF-kB (L. A. Tartaglia, D. V. Goeddel, Immunol Today 13, 151-3 (1992)). Accordingly, TNFR-1 recruits the multivalent adapter molecule TRADD, which like FADD, also contains a death domain (H. Hsu, J. Xiong, D. V. Goeddel, Cell 81, 495-504 (1995); H. Hsu, H.-B. Shu, M.-P. Pan, D. V. Goeddel, Cell 84, 299-308 (1996)). Through its associations with a number of signaling molecules including FADD, TRAF2, and RIP, TRADD can signal both apoptosis and NF-kB activation (H. Hsu, H.-B. Shu, M.-P. Pan, D. V. Goeddel, Cell 84, 299-308 (1996); H. Hsu, J. Huang, H.-B. Shu, V. Baichwal, D. V. Goeddel, Immunity 4, 387-396 (1996)).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

SUMMARY OF THE INVENTION

The present invention provides isolated nucleic acid molecules comprising a polynucleotide encoding at least a portion of a TNFR-6α or -6β polypeptide having the complete amino acid sequences shown in SEQ ID NOS:2 and 4, respectively, or the complete amino acid sequence encoded by a cDNA clone deposited as plasmid DNA as ATCC Deposit Number 97810 and 97809, respectively. The nucleotide sequence determined by sequencing the deposited TNFR-6α and -6β clones, which are shown in FIGS. 1 and 2A-B (SEQ ID NOS:1 and 3, respectively), contain open reading frames encoding complete polypeptides of 300 and 170 amino acid residues, respectively, including an initiation codon encoding an N-terminal methionine at nucleotide positions 25-27 and 73-75 in SEQ ID NOS: 1 and 3, respectively.

The TNFR proteins of the present invention share sequence homology with other TNF receptors. Splice variants TNFR-6α and -6β show the highest degree of sequence homology with the translation products of the human mRNAs for TNFR-I and -II (FIGS. 3A-P) (SEQ ID NOS:5 and 6, respectively) also including multiple conserved cysteine rich domains.

The TNFR-6α and -6β polypeptides have predicted leader sequences of 30 amino acids each; and the amino acid sequence of the predicted mature TNFR-6α and -6β polypeptides are also shown in FIGS. 1 and 2A-B as amino acid residues 31-300 (SEQ ID NO:2) and 31-170 (SEQ ID NO:4), respectively.

Thus, one aspect of the invention provides an isolated nucleic acid molecule comprising a polynucleotide having a nucleotide sequence selected from the group consisting of: (a) a nucleotide sequence encoding a TNFR polypeptide having the complete amino acid sequence in SEQ ID NO:2 or 4, or as encoded by the cDNA clone contained in ATCC Deposit No. 97810 or 97809; (b) a nucleotide sequence encoding a mature TNFR polypeptide having the amino acid sequence at positions 31-300 in SEQ ID NO:2, or 31-170 in SEQ ID NO:4, or as encoded by the cDNA clone contained in ATCC Deposit No. 97810 or 97809; (c) a nucleotide sequence encoding a soluble extracellular domain of a TNFR polypeptide having the amino acid sequence at positions 31 to 283 in SEQ ID NO:2 or 31 to 166 in SEQ ID NO:4, or as encoded by the cDNA clone contained in the ATCC Deposit No. 97810 or 97809; and (d) a nucleotide sequence complementary to any of the nucleotide sequences in (a), (b), or (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c) and (d) above, or a polynucleotide which hybridizes under stringent hybridization conditions to a polynucleotide in (a), (b), (c) or (d), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TNFR polypeptide having an amino acid sequence in (a), (b) or (c), above.

The present invention also relates to recombinant vectors, which include the isolated nucleic acid molecules of the present invention, and to host cells containing the recombinant vectors, as well as to methods of making such vectors and host cells and for using them for production of TNFR polypeptides or peptides by recombinant techniques.

The invention further provides an isolated TNFR polypeptide comprising an amino acid sequence selected from the group consisting of: (a) the amino acid sequence of a full-length TNFR polypeptide having the complete amino acid sequence shown in SEQ ID NO:2 or 4 or as encoded by the cDNA clone contained in ATCC Deposit No. 97810 or 97809; (b) the amino acid sequence of a mature TNFR polypeptide having the amino acid sequence at positions 31-300 in SEQ ID NO:2, or 31-170 in SEQ ID NO:4, or as encoded by the cDNA clone contained in ATCC Deposit No. 97810 or 97809; or (c) the amino acid sequence of a soluble extracellular domain of a TNFR polypeptide having the amino acid sequence at positions 31 to 283 in SEQ ID NO:2 or 31 to 166 in SEQ ID NO:4, or as encoded by the cDNA clone contained in ATCC Deposit No. 97810 or 97809.

The polypeptides of the present invention also include polypeptides having an amino acid sequence at least 80% identical, more preferably at least 90% identical, and still more preferably 95%, 96%, 97%, 98% or 99% identical to those described in (a), (b) or (c) above, as well as polypeptides having an amino acid sequence with at least 90% similarity, and more preferably at least 95% similarity, to those above.

An additional embodiment of this aspect of the invention relates to a peptide or polypeptide which comprises the amino acid sequence of an epitope-bearing portion of a TNFR polypeptide having an amino acid sequence described in (a), (b) or (c), above. Peptides or polypeptides having the amino acid sequence of an epitope-bearing portion of a TNFR polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a TNFR polypeptide having an amino acid sequence described in (a), (b) or (c) above. The invention further provides methods for isolating antibodies that bind specifically to a TNFR polypeptide having an amino acid sequence as described herein. Such antibodies are useful diagnostically or therapeutically as described below.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. The invention also provides for pharmaceutical compositions comprising TNFR polypeptides, particularly human TNFR polypeptides, which may be employed, for instance, to treat infectious disease including HIV infection, endotoxic shock, cancer, autoimmune diseases, graft vs. host disease, acute graft rejection, chronic graft rejection, neurodegenerative disorders, myelodysplastic syndromes, ischemic injury, toxin-induced liver disease, septic shock, cachexia and anorexia. Methods of treating individuals in need of TNFR polypeptides are also provided.

The invention further provides compositions comprising a TNFR polynucleotide or a TNFR polypeptide for administration to cells in vitro, to cells ex vivo and to cells in vivo, or to a multicellular organism. In certain particularly preferred embodiments of this aspect of the invention, the compositions comprise a TNFR polynucleotide for expression of a TNFR polypeptide in a host organism for treatment of disease. Particularly preferred in this regard is expression in a human patient for treatment of a dysfunction associated with aberrant endogenous activity of a TNFR polypeptide.

In another aspect, a screening assay for agonists and antagonists is provided which involves determining the effect a candidate compound has on TNFR polypeptide binding to a TNF-family ligand. In particular, the method involves contacting the TNF-family ligand with a TNFR polypeptide and a candidate compound and determining whether TNFR polypeptide binding to the TNF-family ligand is increased or decreased due to the presence of the candidate compound. In this assay, an increase in binding of a TNFR polypeptide over the standard binding indicates that the candidate compound is an agonist of TNFR polypeptide binding activity and a decrease in TNFR polypeptide binding compared to the standard indicates that the compound is an antagonist of TNFR polypeptide binding activity.

TNFR-6α and -6β are expressed in endothelial cells, keratinocytes, normal prostate and prostate tumor tissue. For a number of disorders of theses tissues or cells, particularly of the immune system, significantly higher or lower levels of TNFR gene expression may be detected in certain tissues (e.g., cancerous tissues) or bodily fluids (e.g., serum, plasma, urine, synovial fluid or spinal fluid) taken from an individual having such a disorder, relative to a "standard" TNFR gene expression level, i.e., the TNFR expression level in healthy tissue from an individual not having the immune system disorder. Thus, the invention provides a diagnostic method useful during diagnosis of such a disorder, which involves: (a) assaying TNFR gene expression level in cells or body fluid of an individual; (b) comparing the TNFR gene expression level with a standard TNFR gene expression level, whereby an increase or decrease in the assayed TNFR gene expression level compared to the standard expression level is indicative of disorder in the immune system.

An additional aspect of the invention is related to a method for treating an individual in need of an increased level of TNFR polypeptide activity in the body comprising administering to such an individual a composition comprising a therapeutically effective amount of an isolated TNFR polypeptide of the invention or an agonist thereof.

A still further aspect of the invention is related to a method for treating an individual in need of a decreased level of TNFR polypeptide activity in the body comprising, administering to such an individual a composition comprising a therapeutically effective amount of a TNFR antagonist. Preferred antagonists for use in the present invention are TNFR-specific antibodies.

BRIEF DESCRIPTION OF THE FIGURES

FIG. 1 shows the nucleotide sequence (SEQ ID NO:1) and deduced amino acid sequence (SEQ ID NO:2) of TNFR-6α.

FIGS. 2A-B show the nucleotide sequence (SEQ ID NO:3) and deduced amino acid sequence (SEQ ID NO:4) of TNFR-6β.

FIGS. 3A-P show an alignment created by the Clustal method using the Megaline program in the DNAstar suite comparing the amino acid sequences of TNFR-6α ("TNFR-6a"), and TNFR-6β ("TNFR-6b") with other TNF receptors, as follows: TNFR1 (SEQ ID NO:5); TNFR2 (SEQ ID NO:6); NGFR (SEQ ID NO:7); LTbR (SEQ ID NO:8); FAS (SEQ ID NO:9); CD27 (SEQ ID NO:10); CD30 (SEQ ID NO:11); CD40 (SEQ ID NO:12); 4-1BB (SEQ ID NO:13); OX40 (SEQ ID NO:14); VC22 (SEQ ID NO:15); and CRMB (SEQ ID NO:16).

FIG. 6 shows the nucleotide sequences of HELDIO6R and HCEOW38R which are related to SEQ ID NOS:1 and 3.

DETAILED DESCRIPTION

Figure 4:
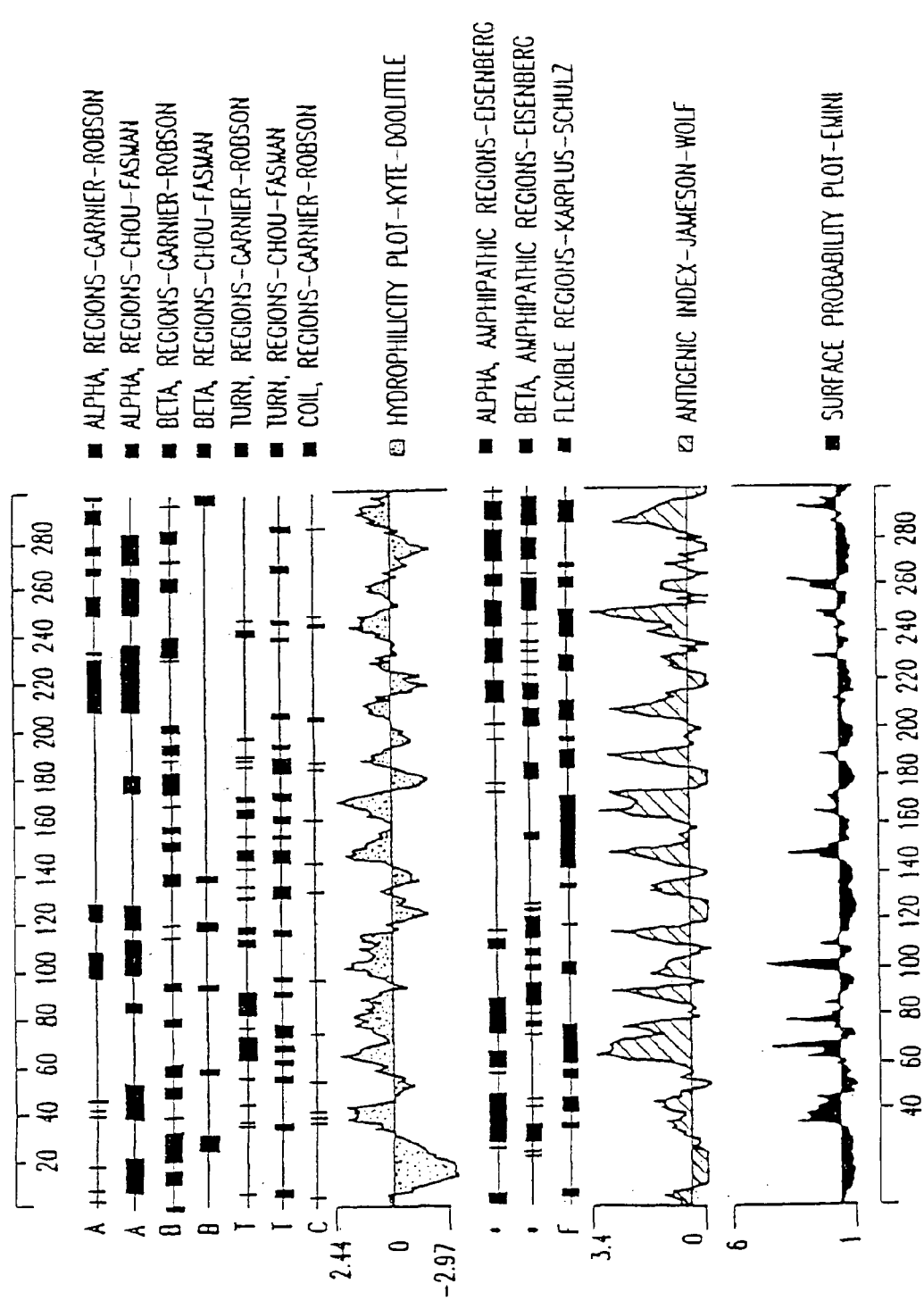
FIGS. 4 and 5 show separate analyses of the TNFR-6α and -6β amino acid sequences, respectively. Alpha, beta, turn and coil regions; hydrophilicity and hydrophobicity; amphipathic regions; flexible regions; antigenic index and surface probability are shown. In the "Antigenic Index—Jameson-Wolf" graphs, the indicate location of the highly antigenic regions of the proteins, i.e., regions from which epitope-bearing peptides of the invention may be obtained.

The present invention provides isolated nucleic acid molecules comprising a polynucleotide encoding a TNFR-6α or -6β polypeptide, generically "TNFR polypeptide(s)" having the amino acid sequence shown in SEQ ID NOS:2 and 4, respectively, which were determined by sequencing cloned cDNAs. The nucleotide sequences shown in FIGS. 1 and 2a-B (SEQ ID NOS:1 and 3) were obtained by sequencing the HPHAE52 and HTPCH84 clones, which were deposited on Nov. 22, 1996 at the American Type Culture Collection, 10801 University Boulevard, Manassas, Virgina 20110-2209 and given accession numbers ATCC 97810 and 97809, respectively. The deposited clones are contained in the pBluescript SK(−) plasmid (Stratagene, La Jolla, Calif.).

Figure 3A:
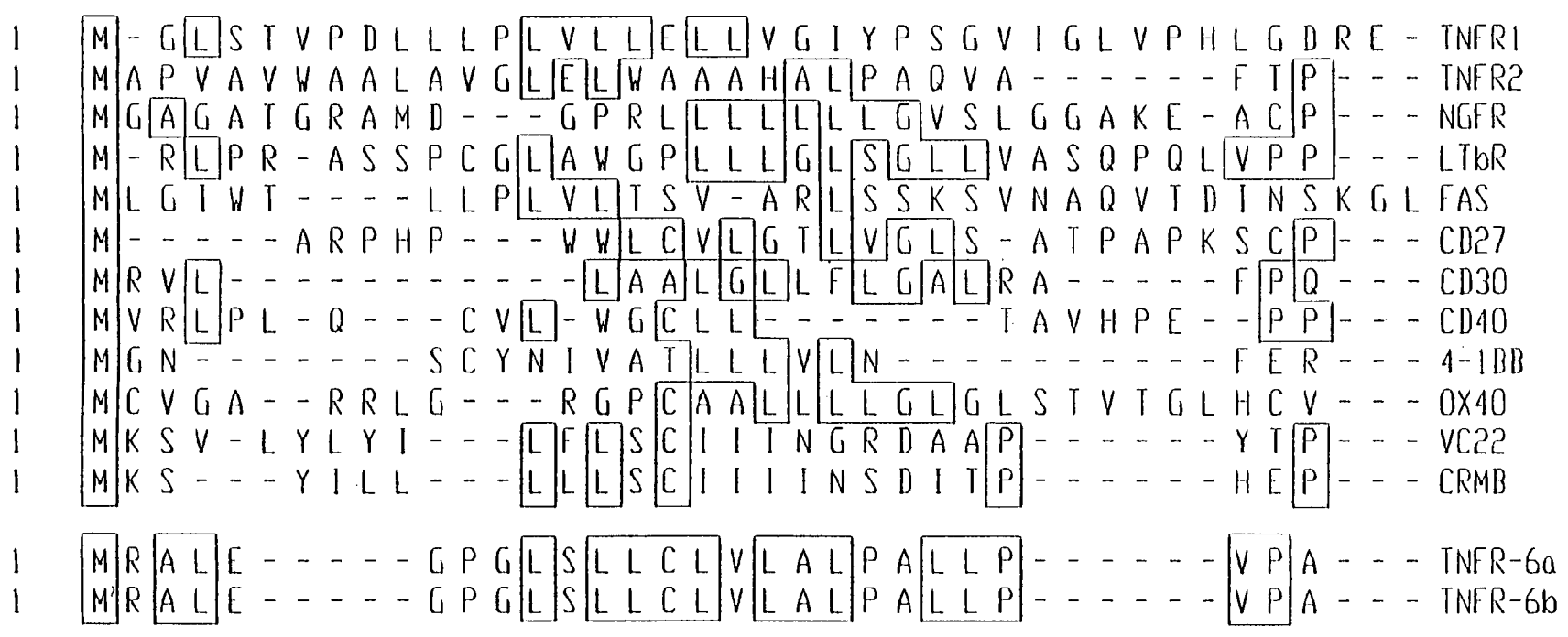
Figure 3B:
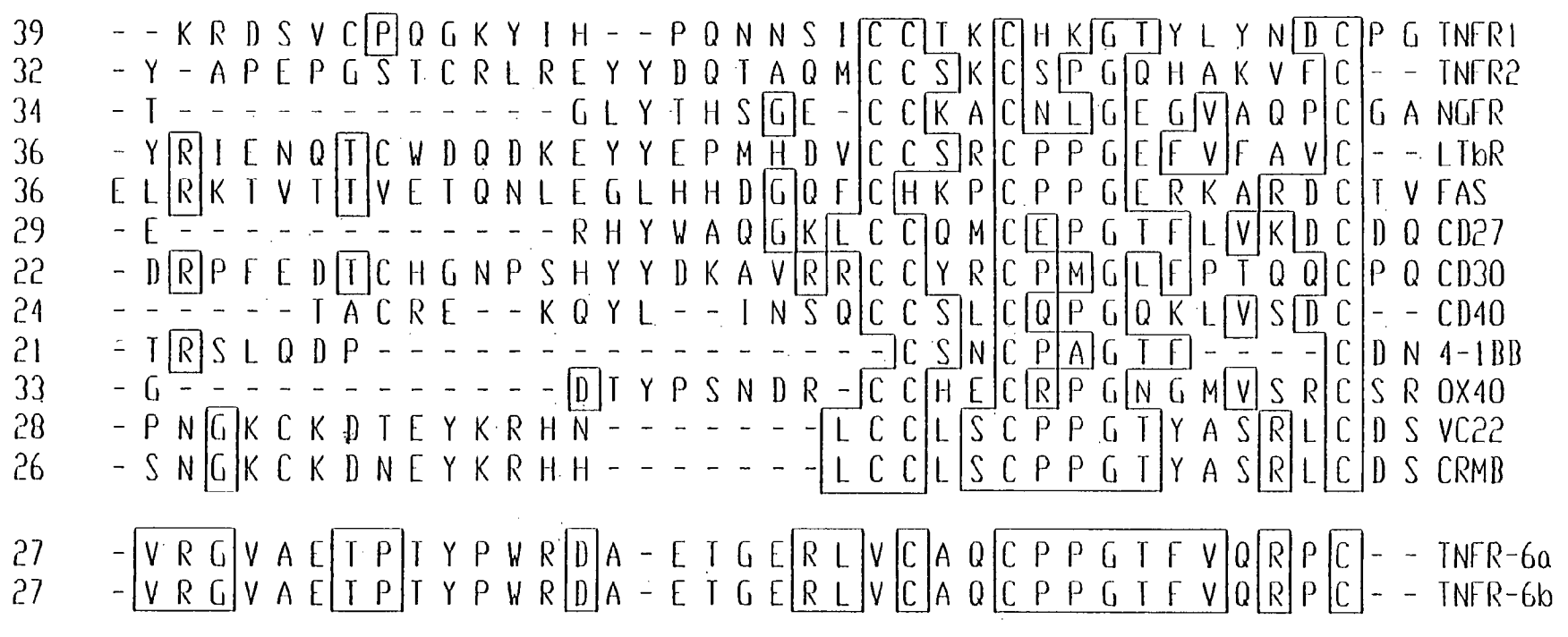
Figure 3C:
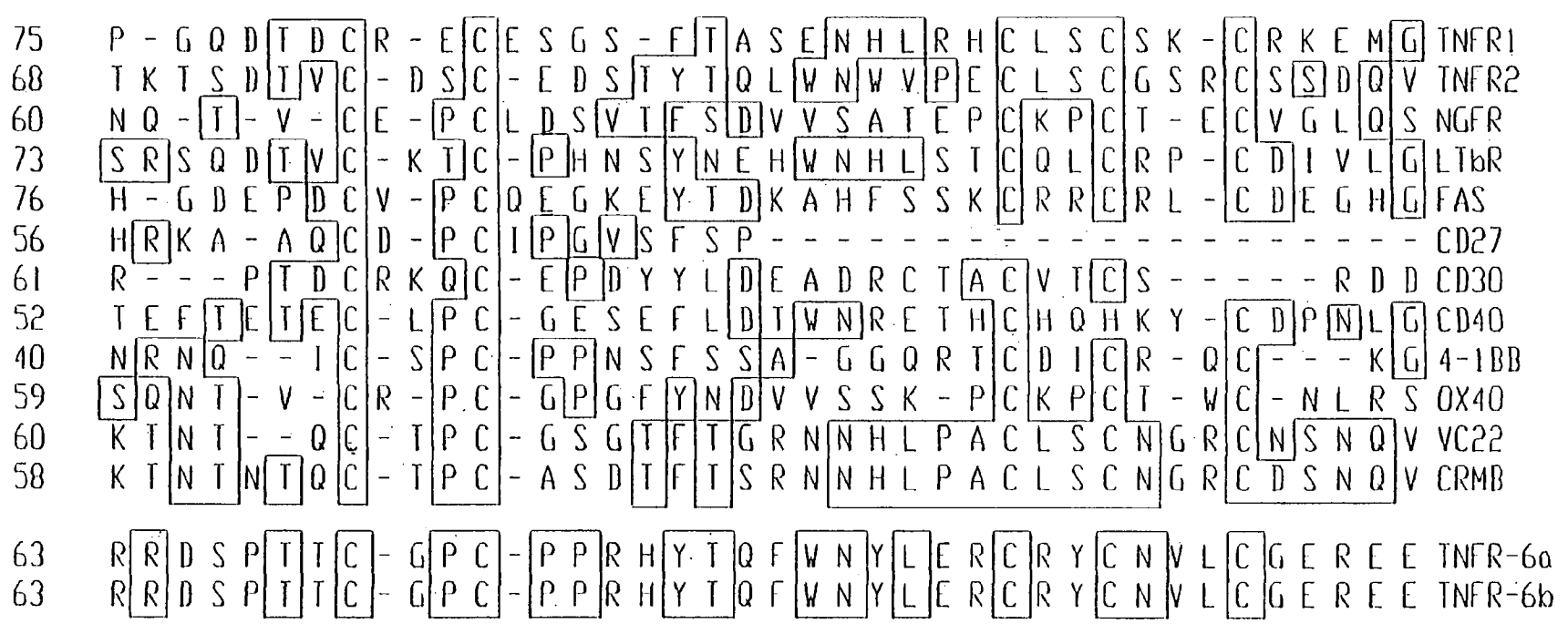
Figure 3D:
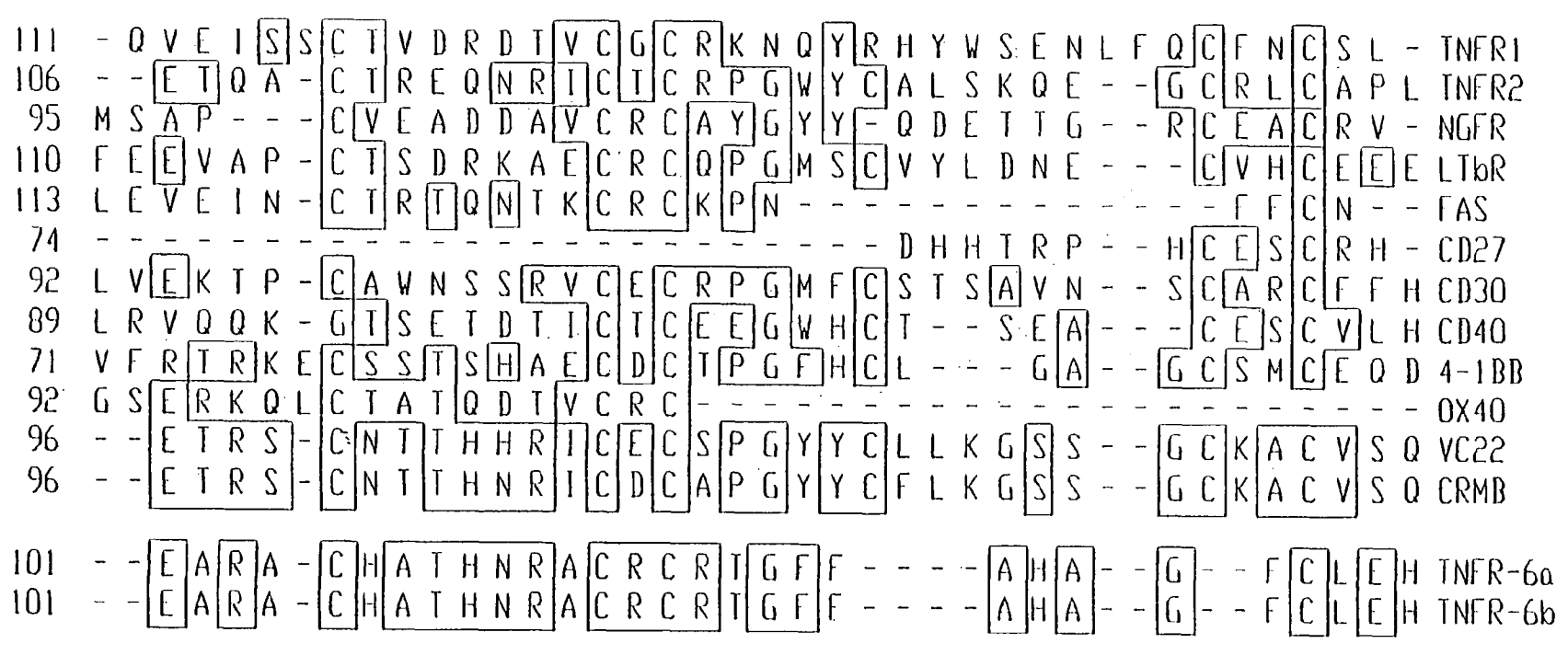
Figure 3E:
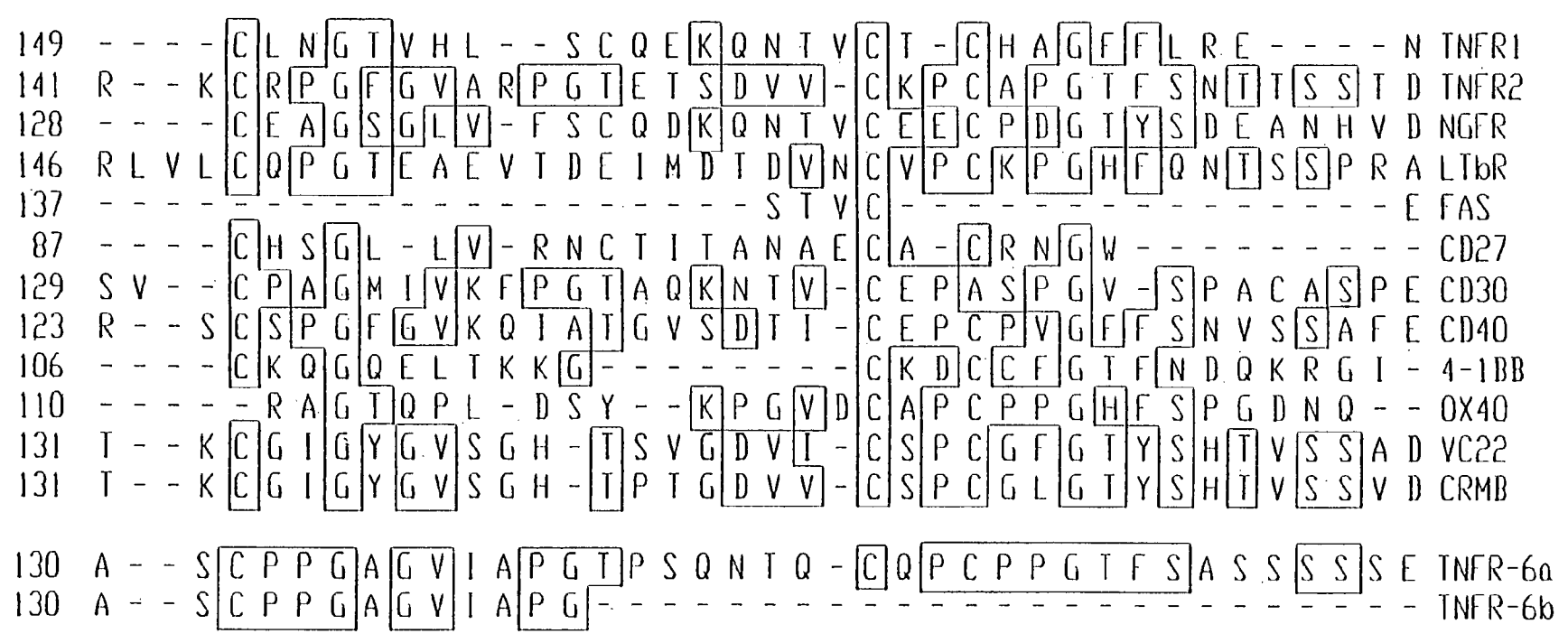
Figure 3F:
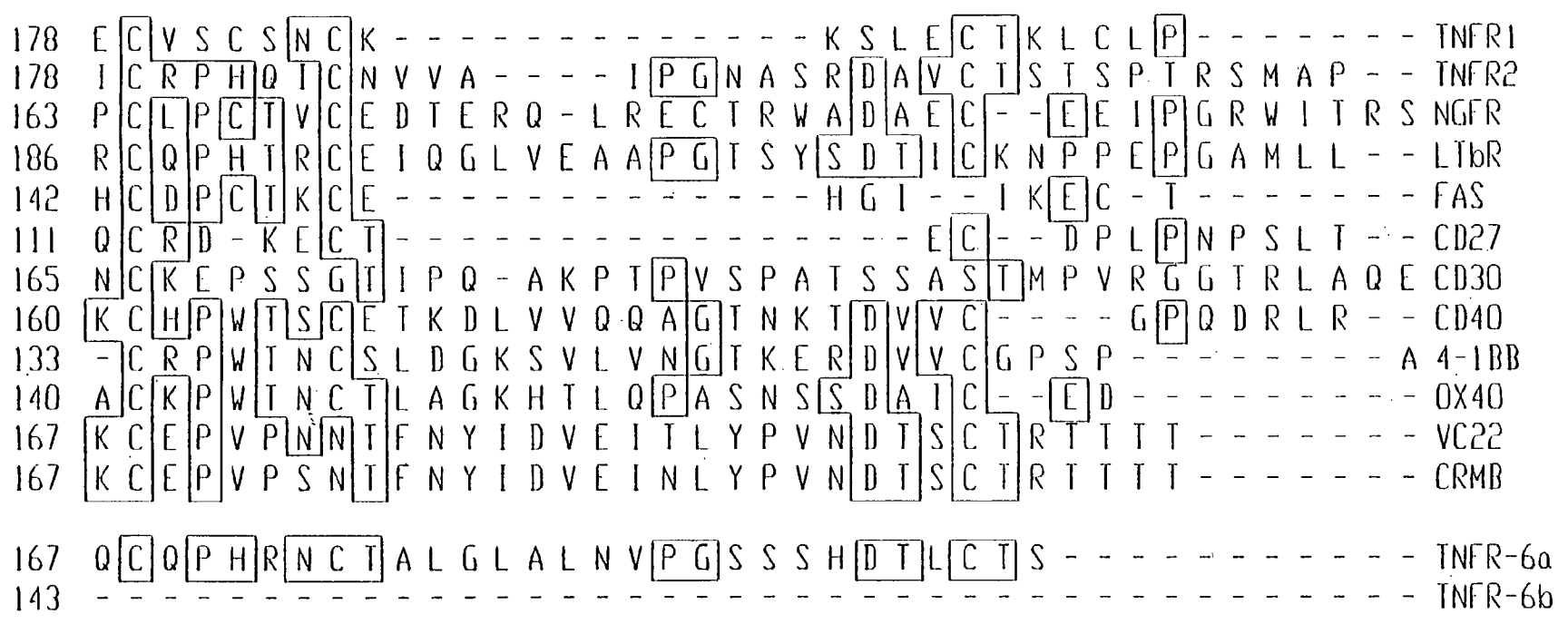
Figure 3G:
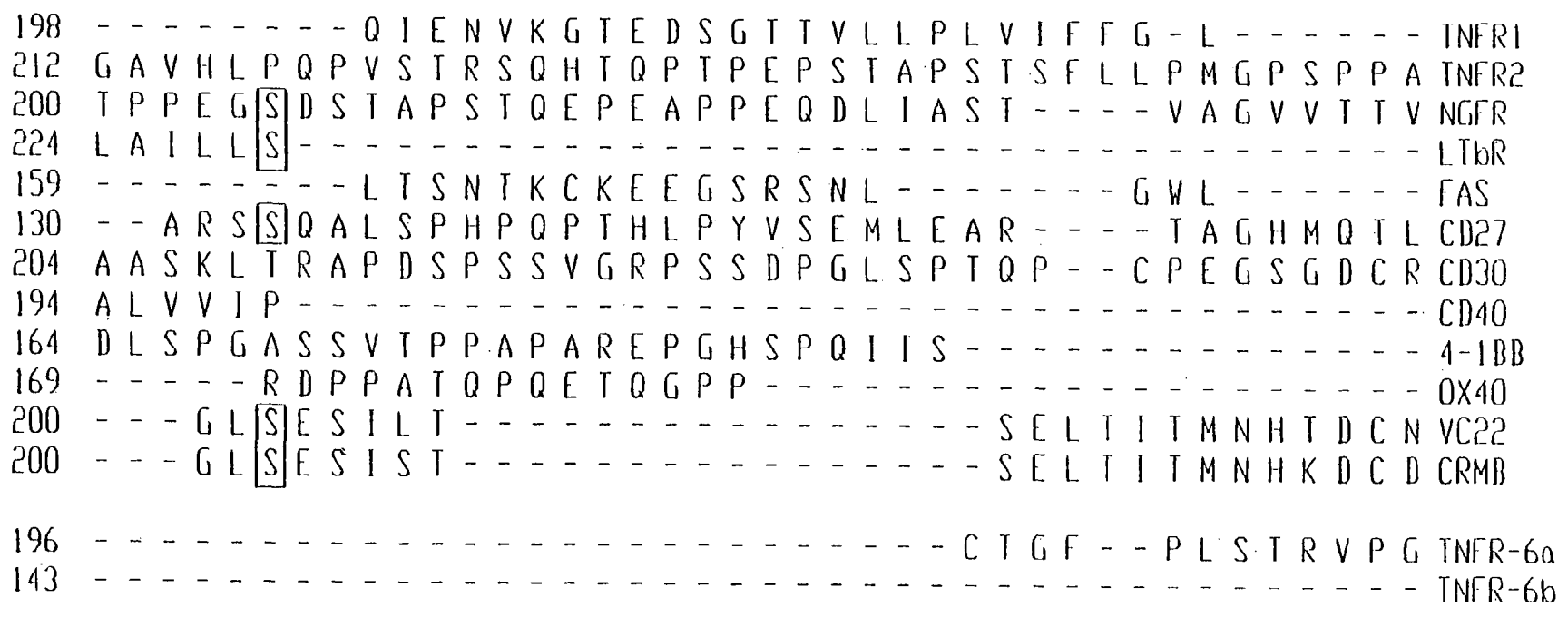
Figure 3J:
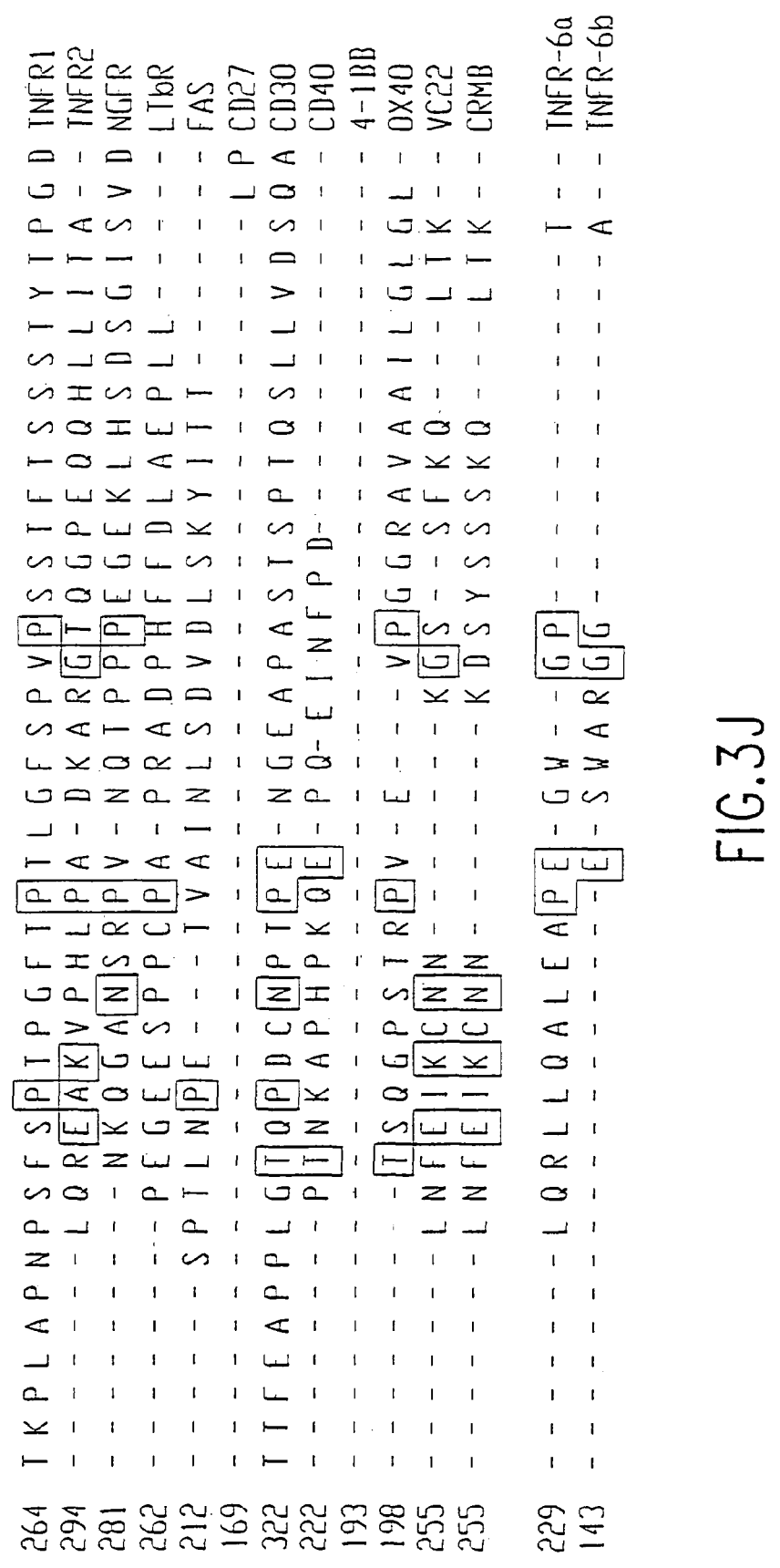
Figure 3M:
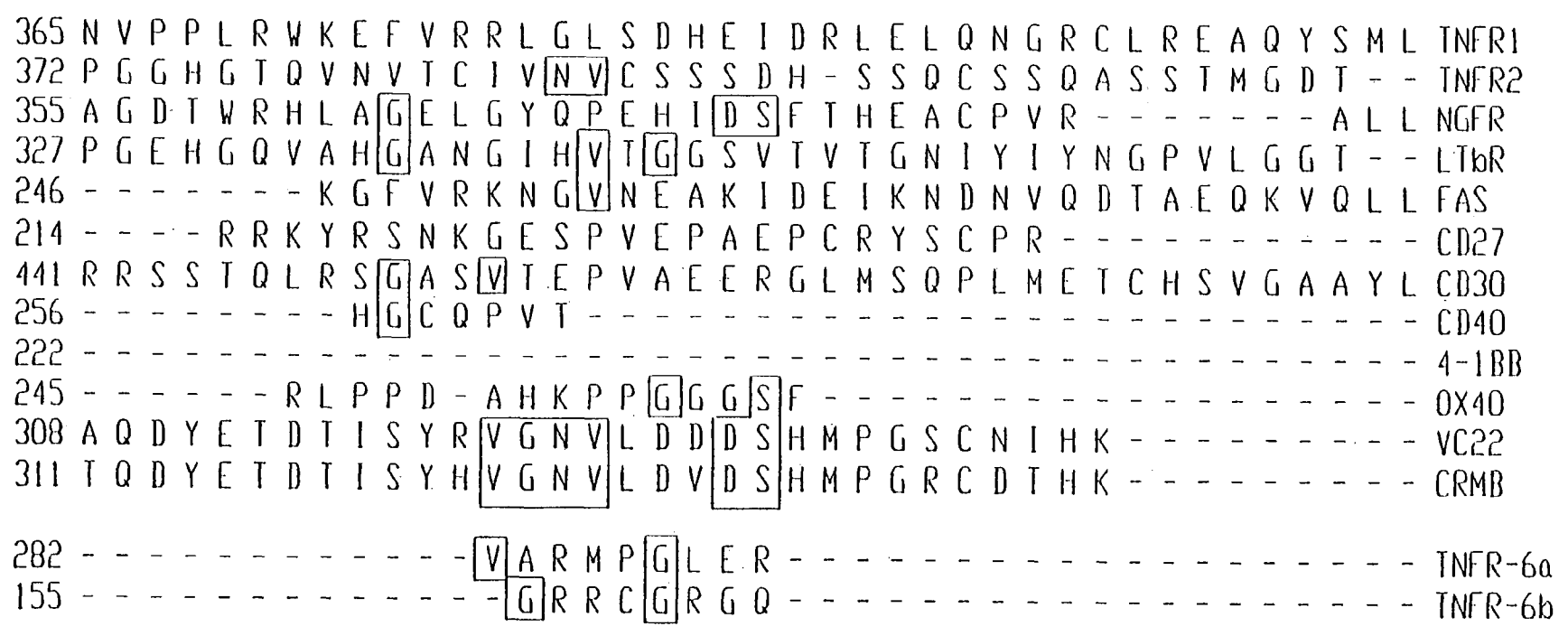

The TNFR-6α and -6β proteins of the present invention are splice variants which share an identical nucleotide and amino acid sequence over the N-terminal 142 residues of the respective proteins. The amino acid sequences of these proteins are about 23% similar to and share multiple conserved cysteine rich domains with the translation product of the human TNFR-2 mRNA (FIGS. 3A-P) (SEQ ID NO:6). Importantly, these proteins share substantial sequence similarity over their extracellular domains including four repeated cysteine rich motifs with significant intersubunit homology. TNFR-2 is thought to exclusively mediate human T-cell proliferation by TNF (PCT WO194/09137).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequences in FIGS. 1 and 2A-B (SEQ ID NOS:1 and 3), a nucleic acid molecule of the present invention encoding a TNFR polypeptide may be obtained using standard cloning and screening procedures, such as those for cloning cDNAs using mRNA as starting material. Illustrative of the invention, the TNFR-6α and -6β clones (FIGS. 1 and 2A-B, respectively) were identified in cDNA libraries from the following tissues: endothelial cells, keratinocytes, normal prostate tissue, and prostate tumor tissue.

The determined nucleotide sequences of the TNFR cDNAs of FIGS. 1 and 2A-B (SEQ ID NOS:1 and 3) contain open reading frames encoding proteins of 300 and 170 amino acid residues, with an initiation codon at nucleotide positions 25-27 and 73-75 of the nucleotide sequences in FIGS. 1 and 2A-B (SEQ ID NOS:1 and 3), respectively.

The open reading frames of the TNFR-6α and -6β genes share sequence homology with the translation product of the human mRNA for TNFR-2, including the soluble extracellular domain of about residues 31-283 of SEQ ID NO:2 and 31-166 of SEQ ID NO:4, respectively.

As one of ordinary skill would appreciate, due to the possibilities of sequencing errors discussed above, the actual complete TNFR polypeptides encoded by the deposited cDNAs, which comprise about 300 and 170 amino acids, may be somewhat longer or shorter. More generally, the actual open reading frames may be anywhere in the range of ±20 amino acids, more likely in the range of ±10 amino acids, of that predicted from the first methionine codon from the N-terminus shown in FIGS. 1 and 2A-B (SEQ ID NOS:1 and 3), which is in-frame with the translated sequences shown in each respective figure. It will further be appreciated that, depending on the analytical criteria used for identifying various functional domains, the exact "address" of the extracellular and transmembrane domain(s) of the TNFR polypeptides may differ slightly from the predicted positions above. For example, the exact location of the extracellular domain in SEQ ID NO:2 may vary slightly (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domains of the TNFR-6α & -6β proteins.

Leader and Mature Sequences

The amino acid sequences of the complete TNFR proteins include a leader sequence and a mature protein, as shown in SEQ ID NOS:2 and 4. More in particular, the present invention provides nucleic acid molecules encoding mature forms of the TNFR proteins. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding a mature TNFR polypeptide having the amino acid sequence encoded by a cDNA clone identified as ATCC Deposit No. 97810 or 97809. By the "mature TNFR polypeptides having the amino acid sequence encoded by a cDNA clone in ATCC Deposit No. 97810, or 97809" is meant the mature form(s) of the protein produced by expression in a mammalian cell (e.g., COS cells, as described below) of the complete open reading frame encoded by the human DNA sequence of the clone contained in the deposited vector.

In addition, methods for predicting whether a protein has a secretory leader as well as the cleavage point for that leader sequence are available. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75-80% (von Heinje, supra). However, the two methods do not always produce the same predicted cleavage point(s) for a given protein.

In the present case, the deduced amino acid sequence of the complete TNFR polypeptides were analyzed by a computer program "PSORT", available from Dr. Kenta Nakai of the Institute for Chemical Research, Kyoto University (see K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis of the TNFR amino acid sequences by this program provided the following results: TNFR-6α & -6β encode mature polypeptides having the amino acid sequences of residues 31-300 and 31-170 of SEQ ID NOS:2 and 4, respectively.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 25-27 73-75 of the nucleotide sequences shown in SEQ ID NOS:1 and 3, respectively.

Also included are DNA molecules comprising the coding sequence for the predicted mature TNFR polypeptides shown at positions 31-300 and 31-170 of SEQ ID NOS:2 and 4, respectively.

In addition, isolated nucleic acid molecules of the invention include DNA molecules which comprise a sequence substantially different from those described above but which, due to the degeneracy of the genetic code, still encode a TNFR protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding a TNFR polypeptide having an amino acid sequence encoded by the cDNA clone contained in the plasmid deposited as ATCC Deposit No. 97810 or 97809. Preferably, this nucleic acid molecule will encode the mature polypeptide encoded by the above-described deposited cDNA clone.

The invention further provides an isolated nucleic acid molecule having the nucleotide sequence shown in FIG. 1 or 2A-B (SEQ ID NO:1 or 3) or the nucleotide sequence of the TNFR cDNAs contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the TNFR genes in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides polynucleotides having a nucleotide sequence representing the portion of SEQ ID NO:1 or 3 which consist of positions 25-924 and 73-582 of SEQ ID NOS:1 and 3, respectively. Also contemplated are polynucleotides encoding TNFR polypeptides which lack an amino terminal methionine such polynucleotides having a nucleotide sequence representing the portion of SEQ ID NOS:1 and 3 which consist of positions 28-924 and 76-582, respectively. Polypeptides encoded by such polynucleotides are also provided, such polypeptides comprising an amino acid sequence at positions 2-300 and 2-170 of SEQ ID NOS:2 and 4, respectively.

In addition, the invention provides nucleic acid molecules having nucleotide sequences related to extensive portions of SEQ ID NOS:1 and 3 as follows: HELDIO6R (SEQ ID NO:17) and HCEOW38R (SEQ ID NO:18) are related to both SEQ ID NOS:1 and 3. Preferred are polypeptide fragments of SEQ ID NOS:1 and 3 which are not SEQ ID NO:19 or 20 or subfragments of either SEQ ID NO:19 or 20. The sequences of HELDIO6R and HCEOW38R are shown in FIG. 6.

More generally, by a fragment of an isolated nucleic acid molecule having the nucleotide sequence of the deposited cDNA or the nucleotide sequence shown in FIGS. 1 or 2A-B (SEQ ID NOS:1 or 3) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50-300 nt in length are also useful according to the present invention as are fragments corresponding to most, if not all, of the nucleotide sequence of the deposited cDNAs or as shown in FIGS. 1 and 2A-B (SEQ ID NOS:1 and 3). Especially preferred are fragments comprising at least 500 nucleotides which are at least 95% identical to 500 contiguous nucleotides shown in SEQ ID NO:1. By a fragment at least 20 nt in length, for example, is intended fragments which include 20 or more contiguous bases from the nucleotide sequence of a deposited cDNA or the nucleotide sequence as shown in FIGS. 1 and 2A-B (SEQ ID NOS:1 and 3). Preferred nucleic acid fragments of the present invention include nucleic acid molecules encoding epitope-bearing portions of the TNFR polypeptides as identified in FIGS. 4 and 5 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, a cDNA clone contained in ATCC Deposit No. 97810 or 97809. By "stringent hybridization conditions" is intended overnight incubation at 42° C. in a solution comprising: 50% formamide, 5×SSC (750 mM NaCl, 75 mM trisodium citrate), 50mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., a deposited cDNA or a nucleotide sequence as shown in FIG. 1 or 2A-B (SEQ ID NO:1 or 3)). Of course, a polynucleotide which hybridizes only to a poly A sequence (such as the 3' terminal poly(A) tract of a TNFR cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a TNFR polypeptide may include, but are not limited to those encoding the amino acid sequence of the mature polypeptide, by itself; and the coding sequence for the mature polypeptide and additional sequences, such as those encoding the about 26-35 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37: 767 (1984). As discussed below, other such fusion proteins include a TNFR-5, -6α or -6β fused to Fc at the N- or C-terminus.

Variant and Mutant Polynucleotides

The present invention further relates to variants of the nucleic acid molecules of the present invention, which encode portions, analogs or derivatives of a TNFR polypeptide. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the TNFR polypeptide or portions thereof. Also especially preferred in this regard are conservative substitutions.

Highly preferred are nucleic acid molecules encoding a mature protein having an amino acid sequence shown in SEQ ID NOS:2 and 4 or the mature TNFR polypeptide sequences encoded by the deposited cDNA clones.

Most highly preferred are nucleic acid molecules encoding the extracellular domain of a protein having the amino acid sequence shown in SEQ ID NO:2 or 4 or the extracellular domain of a TNFR amino acid sequence encoded by a deposited cDNA clone.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding a TNFR polypeptide having the complete amino acid sequence in SEQ ID NO:2 or 4, or as encoded by a cDNA clone contained in ATCC Deposit No. 97810 or 97809; (b) a nucleotide sequence encoding a mature TNFR polypeptide having an amino acid sequence at positions 31-300 or 31-170 in SEQ ID NO:2 or 4, respectively, or as encoded by a cDNA clone contained in ATCC Deposit No. 97810 or 97809; (c) a nucleotide sequence encoding a soluble extracellular domain of a TNFR polypeptide having the amino acid sequence at positions 31-283 and 31-166 of SEQ ID NOS:2 and 4, respectively; and (d) a nucleotide sequence complementary to any of the nucleotide sequences in (a), (b) or (c) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), or (d), above, or a polynucleotide which hybridizes under stringent hybridization conditions to a polynucleotide in (a), (b), (c), or (d), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a TNFR polypeptide having an amino acid sequence in (a), (b), (c) or (d), above.

The present invention also relates to recombinant vectors, which include the isolated nucleic acid molecules of the present invention, and to host cells containing the recombinant vectors, as well as to methods of making such vectors and host cells and for using them for production of TNFR polypeptides or peptides by recombinant techniques.

By a polynucleotide having a nucleotide sequence at least, for example, 95% "identical" to a reference nucleotide sequence encoding a TNFR polypeptide is intended that the nucleotide sequence of the polynucleotide is identical to the reference sequence except that the polynucleotide sequence may include up to five point mutations per each 100 nucleotides of the reference nucleotide sequence encoding the TNFR polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, a nucleotide sequence shown in FIG. 1 to or 2A-B, or to the nucleotides sequence of a deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96% 97%, 98% or 99% identical to a nucleic acid sequence shown in FIG. 1 or 2A-B (SEQ ID NO:1 and 3) or to the nucleic acid sequence of a deposited cDNA, irrespective of whether they encode a polypeptide having TNFR activity. This is because even where a particular nucleic acid molecule does not encode a polypeptide having TNFR activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TNFR activity include, inter alia, (1) isolating a TNFR gene or allelic variants thereof in a cDNA library; (2) in situ hybridization (e.g., "FISH") to metaphase chromosomal spreads to provide precise chromosomal location of the TNFR gene, as described in Verma et al., Human Chromosomes: A Manual of Basic Techniques, Pergamon Press, New York (1988); and Northern Blot analysis for detecting TNFR mRNA expression in specific tissues.

Preferred, however, are nucleic acid molecules having sequences at least 90%, 95%, 96% 97%, 98% or 99% identical to a nucleic acid sequence shown in FIG. 1 or 2A-B (SEQ ID NOS:1 and 3) or to the nucleic acid sequence of a deposited cDNA which do, in fact, encode polypeptides having TNFR protein activity. By "a polypeptide having TNFR activity" is intended polypeptides exhibiting activity similar, but not necessarily identical, to an activity of a mature or extracellular forms of a TNFR-6α or -6β protein of the invention, as measured in a particular biological assay. The TNF family ligands induce various cellular responses by binding to TNF-family receptors, including the TNFR-6α and -6β of the present invention. Cells which express the TNFR proteins are believed to have a potent cellular response to TNFR-I receptor ligands including B lymphocytes (CD19+), both CD4 and CD8+ T lymphocytes, monocytes and endothelial cells. By a "cellular response to a TNF-family ligand" is intended any genotypic, phenotypic, and/or morphological change to a cell, cell line, tissue, tissue culture or patient that is induced by a TNF-family ligand. As indicated, such cellular responses include not only normal physiological responses to TNF-family ligands, but also diseases associated with increased cell proliferation or the inhibition of increased cell proliferation, such as by the inhibition of apoptosis.

Screening assays for the forgoing are known in the art. One such screening assay involves the use of cells which express the receptor (for example, transfected CHO cells) in a system which measures extracellular pH changes caused by receptor activation, for example, as described in Science 246:181-296 (October 1989). For example, a TNF-family ligand may be contacted with a cell which expresses the mature form of the receptor polypeptide of the present invention and a second messenger response, e.g., signal transduction or pH changes, may be measured to determine whether the TNFR polypeptide is active.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of a deposited cDNA or the nucleic acid a sequence shown in FIG. 1 or 2A-B (SEQ ID NO:1 and 3) will encode a polypeptide "having TNFR protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having TNFR protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of TNFR polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art. Among vectors preferred for use in bacteria include pQE70, pQE60 and pQE-9, available from QIAGEN, Inc., supra; Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986). The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52-58 (1995) and K. Johanson et al., *J. Biol. Chem.* 270:9459-9471 (1995).

The TNFR proteins can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Polypeptides and Fragments

The invention further provides isolated TNFR polypeptides having the amino acid sequences encoded by the deposited cDNAs, or the amino acid sequences in SEQ ID NOS:2 and 4, or a peptide or polypeptide comprising a portion of the above polypeptides.
Variant and Mutant Polypeptides To improve or alter the characteristics of a TNFR polypeptide, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.
N-Terminal and C-Terminal Deletion Mutants For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984-2988 (1993) reported modified KGF proteins that had heparin binding activity even if 3, 8, or 27 amino-terminal amino acid residues were missing. In the present case, since the proteins of the invention are members of the TNFR polypeptide family, deletions of N-terminal amino acids up to the Cysteine at position 49 of SEQ ID NOS:2 and 4 (TNFR-6α and -6β) may retain some biological activity such as regulation of proliferation and apoptosis of lymphoid cells. Polypeptides having further N-terminal deletions including the C49 residue in SEQ ID NOS:2 and 4, would not be expected to retain such biological activities because it is known that these residues in a TNFR-related polypeptide are required for forming a disulfide bridge to provide structural stability which is needed for receptor binding and signal transduction.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or extracellular domain of the TNFR protein generally will be retained when less than the majority of the residues of the complete protein or extracellular domain are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the TNFR shown in SEQ ID NOS:2 and 4, up to the cysteine residue at position number 49, and polynucleotides encoding such polypeptides. In particular, the present invention provides TNFR-5 polypeptides comprising the amino acid sequence of residues m-300 and n-170 of SEQ ID NOS:2 and 4, respectively where m and n are integers in the range of 1-49 where 49 is the position of the first cysteine residue from the N-terminus of the complete TNFR-6α and -6β polypeptides (shown in SEQ ID NOS:2 and 4, respectively) believed to be required for activity of the TNFR-6α and -6β proteins.

More in particular, the invention provides polynucleotides encoding polypeptides having the amino acid sequence of residues: 1-300, 2-300, 3-300, 4-300, 5-300, 6-300, 7-300, 8-300, 9-300, 10-300, 11-300, 12-300, 13-300, 14-300, 15-300, 16-300, 17-300, 18-300, 19-300, 20-300, 21-300, 22-300, 23-300, 24-300, 25-300, 26-300, 27-300, 28-300, 29-300, 30-300, 31-300, 32-300, 33-300, 34-300, 35-300, 36-300, 37-300, 38-300, 39-300, 40-300, 41-300, 42-300, 43-300, 44-300, 45-300, 46-300, 47-300, 48-300, and 49-300 of SEQ ID NO:2; and 1-170, 2-170, 3-170, 4-170, 5-170, 6-170, 7-170, 8-170, 9-170, 10-170, 11-170, 12-170, 13-170, 14-170, 15-170, 16-170, 17-170, 18-170, 19-170, 20-170, 21-170, 22-170, 23-170, 24-170, 25-170, 26-170, 27-170, 28-170, 29-170, 30-170, 31-170, 32-170, 33-170, 34-170, 35-170, 36-170, 37-170, 38-170, 39-170, 40-170, 41-170, 42-170, 43-170, 44-170, 45-170, 46-170, 47-170, 48-170, and 49-170 of SEQ ID NO:4. Polynucleotides encoding these polypeptides also are provided.

Similarly, many examples of biologically functional C-terminal deletion muteins are known. For instance, interferon gamma shows up to ten times higher activities by deleting 8-10 amino acid residues from the carboxy terminus of the protein (Döbeli et al., *J. Biotechnology* 7:199-216 (1988)). In the present case, since the protein of the invention is a member of the TNFR polypeptide family, deletions of C-terminal amino acids up to the cysteine at position 193 and 132 of SEQ ID NOS:2 and 4, respectively, may retain some biological activity such as regulation of proliferation and apoptosis of lymphoid cells. Polypeptides having further C-terminal deletions including the cysteines at positions 193 and 132 of SEQ ID NOS:2 and 4, respectively, would not be expected to retain such biological activities because it is known that these residues in TNF receptor-related polypeptides are required for forming disulfide bridges to provide structural stability which is needed for receptor binding.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature form protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of TNFR-6α and -6β shown in SEQ ID NOS:2 and 4 up to the cysteine at position 193 and 132 of SEQ ID NOS:2 and 4, respectively, and polynucleotides encoding such polypeptides. In particular, the present invention provides polypeptides having the amino acid sequence of residues 1-y and 1-z of the amino acid sequence in SEQ ID NOS:2 and 4, respectively, where y is any integer in the range of 193-300 and z is any integer in the range of 132-170. Polynucleotides encoding these polypeptides also are provided.

The invention also provides polypeptides having one or more amino acids deleted from both the amino and the carboxyl termini, which may be described generally as having residues m-y of SEQ ID NO:2 and n-z of SEQ ID NO:4, where m, n, y and z are integers as described above.

Also included are a nucleotide sequence encoding a polypeptide consisting of a portion of a complete TNFR amino acid sequence encoded by a UI cDNA clone contained in ATCC Deposit No. 97810, or 97809, where this portion excludes from 1 to about 49 amino acids from the amino terminus of the complete amino acid sequence encoded by the cDNA clone contained in ATCC Deposit No. 97810 and 97809, respectively, or from 1 to about 107 or 58 amino acids from the carboxy terminus of the complete amino acid sequence encoded by the cDNA clone contained in ATCC Deposit No. 97810 and 97809, respectively, or any combination of the above amino terminal and carboxy terminal deletions, of the complete amino acid sequence encoded by the cDNA clone contained in ATCC Deposit No. 97810 or 97809. Polynucleotides encoding all of the above deletion mutant polypeptide forms also are provided.

Other Mutants

In addition to terminal deletion forms of the protein discussed above, it also will be recognized by one of ordinary skill in the art that some amino acid sequences of the TNFR polypeptides can be varied without significant effect on the structure or function of the proteins. If such differences in sequence are contemplated, it should be remembered that there will be critical areas on the protein which determine activity.

Thus, the invention further includes variations of the TNFR polypeptides which show substantial TNFR polypeptide activity or which include regions of TNFR protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the fragment, derivative or analog of the polypeptide of SEQ ID NO:2, 4 or 6, or that encoded by a deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature or soluble extracellular polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the TNFR of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the TNFR proteins of the present invention that are essential for function can be identified by methods known in the art, such as site-directed mutagenesis or alanine-scanning mutagenesis (Cunningham and Wells, Science 244: 1081-1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).

Replacement of amino acids can also change the selectivity of the binding of a ligand to cell surface receptors. For example, Ostade et al., Nature 361:266-268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., J. Mol. Biol. 224:899-904 (1992) and de Vos et al. Science 255:306-312 (1992)).

Since TNFR-6α and -6β are members of the TNF receptor-related protein family, to modulate rather than completely eliminate biological activities of TNFR preferably mutations are made in sequences encoding amino acids in the TNFR conserved extracellular domain, more preferably in residues within this region which are not conserved among members of the TNF receptor family. Also forming part of the present invention are isolated polynucleotides comprising nucleic acid sequences which encode the above TNFR mutants.

The polypeptides of the present invention are preferably provided in an isolated form, and preferably are substantially purified. A recombinantly produced version of the TNFR polypeptides can be substantially purified by the one-step method described in Smith and Johnson, Gene 67:31-40 (1988). Polypeptides of the invention also can be purified from natural or recombinant sources using anti-TNFR-6α and -6β antibodies of the invention in methods which are well known in the art of protein purification.

The invention further provides isolated TNFR polypeptides comprising an amino acid sequence selected from the group consisting of: (a) the amino acid sequence of a full-length TNFR polypeptide having the complete amino acid sequence shown in SEQ ID NO:2 or 4 or as encoded by a cDNA clone contained in ATCC Deposit No. 97810 or 97809; (b) the amino acid sequence of a mature TNFR polypeptide having the amino acid sequence at positions 31-300 in SEQ ID NO:2 or 31-170 in SEQ ID NO:4, or as encoded by a cDNA clone contained in ATCC Deposit No. 97810 or 97809; or (c) the amino acid sequence of a soluble extracellular domain of a TNFR polypeptide having the amino acid sequence at positions 31 to 283 in SEQ ID NO:2 or 31 to 166 in SEQ ID NO:4, or as encoded by the cDNA clone contained in ATCC Deposit No. 97810 or 97809.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2 or 4, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of a TNFR polypeptide is intended that the amino acid sequence of the polypeptide is identical to the reference sequence except that the polypeptide sequence may include up to five amino acid alterations per each 100 amino acids of the reference amino acid of the TNFR polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or 4, or to an amino acid sequence encoded by a deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting TNFR protein expression as described below or as agonists and antagonists capable of enhancing or inhibiting TNFR protein function. Further, such polypeptides can be used in the yeast two-hybrid system to "capture" TNFR protein binding proteins which are also candidate agonists and antagonists according to the present invention. The yeast two hybrid system is described in Fields and Song, Nature 340: 245-246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science,* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777.

Figure 5:
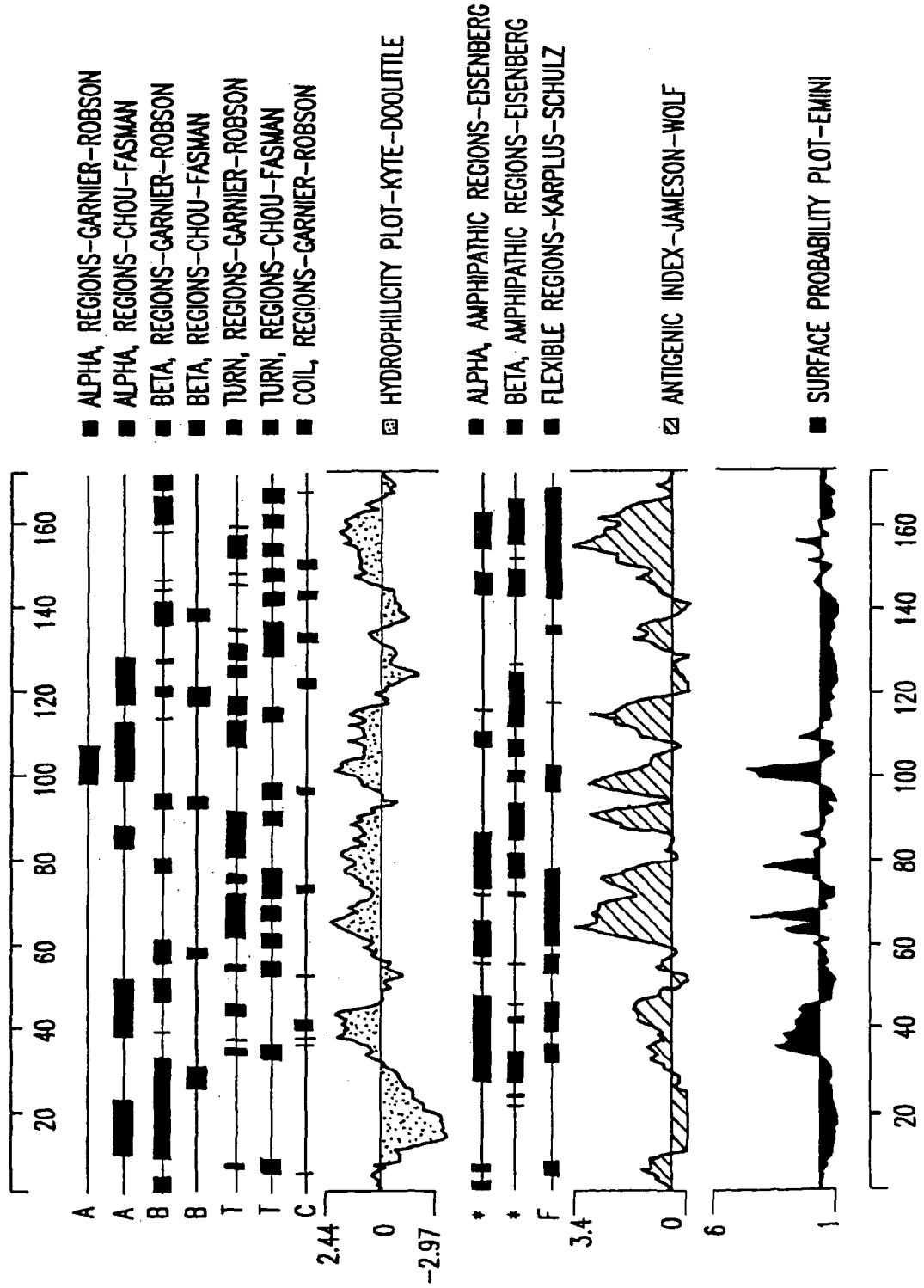

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate TNFR-specific antibodies include: a polypeptide comprising amino acid residues from about Ala-31 to about Thr-46, from about Phe-57 to about Thr-117, from about Cys-132 to about Thr-175, from about Gly-185 to about Thr-194, from about Val-205 to about Asp-217, from about Pro-239 to about Leu-264, and from about Ala-283 to about Pro-298 in SEQ ID NO:2; and from about Ala-31 to about Thr-46, from about Phe-57 to about Gln-80, from about Glu-86 to about His-106, from about Thr-108 to about Phe-119, from about His-129 to about Val-138, and from about Gly-142 to about Pro-166 in SEQ ID NO:4. These polypeptide fragments have been determined to bear antigenic epitopes of the TNFR-6α and -6β polypeptides respectively, by the analysis of the Jameson-Wolf antigenic index, as shown in FIGS. 4 and 5, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131-5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910-914; and Bittle, F. J. et al., *J. Gen. Virol.* 66:2347-2354 (1985). Immunogenic epitope-bearing peptides of the invention, i.e., those parts of a protein that elicit an antibody response when the whole protein is the immunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, TNFR polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84-86 (1988)). Fusion proteins that have a disulfide-linked dimeric structure due to the IgG part can also be more efficient in binding and neutralizing other molecules than the monomeric TNFR protein or protein fragment alone (Fountoulakis et al., *J. Biochem.* 270:3958-3964 (1995)).

Antibodies

TNFR-protein specific antibodies for use in the present invention can be raised against the intact TNFR-6α and -6β proteins or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to a TNFR protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the TNFR protein or an antigenic fragment thereof can be administered to an animal in order to induce the production of sera containing polyclonal antibodies. In a preferred method, a preparation of TNFR protein is prepared and purified to render it substantially free of natural contaminants. Such a preparation is then introduced into an animal in order to produce polyclonal antisera of greater specific activity.

In the most preferred method, the antibodies of the present invention are monoclonal antibodies. Such monoclonal antibodies can be prepared using hybridoma technology (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., (1981) pp. 563-681). In general, such procedures involve immunizing an animal (preferably a mouse) with a TNFR protein antigen or, more preferably, with a TNFR protein-expressing cell. Suitable cells can be recognized by their capacity to bind anti-TNFR-6α or -6β protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, Manasses, Va. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the desired TNFR antigen.

Alternatively, additional antibodies capable of binding to the TNFR antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, TNFR-protein specific antibodies are used to immunize an animal, preferably a mouse. The splenocytes of such an animal are then used to produce hybridoma cells, and the hybridoma cells are screened to identify clones which produce an antibody whose ability to bind to the TNFR protein-specific antibody can be blocked by the TNFR protein antigen. Such antibodies comprise anti-idiotypic antibodies to the TNFR protein-specific antibody and can be used to immunize an animal to induce formation of further TNFR protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, TNFR protein-binding fragments can be produced through the application of recombinant DNA technology or through synthetic chemistry.

For in vivo use of anti-TNFR in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Immune System-Related Disorders

Diagnosis

The present inventors have discovered that TNFR-6α and -6β are expressed in hematopoeitic and transformed tissues. For a number of immune system-related disorders, substantially altered (increased or decreased) levels of TNFR gene expression can be detected in immune system tissue or other cells or bodily fluids (e.g., sera and plasma) taken from an individual having such a disorder, relative to a "standard" TNFR gene expression level, that is, the TNFR expression level in immune system tissues or bodily fluids from an individual not having the immune system disorder. Thus, the invention provides a diagnostic method useful during diagnosis of an immune system disorder, which involves measuring the expression level of the gene encoding the TNFR protein in immune system tissue or other cells or body fluid from an individual and comparing the measured gene expression level with a standard TNFR gene expression level, whereby an increase or decrease in the gene expression level compared to the standard is indicative of an immune system disorder.

In particular, it is believed that certain tissues in mammals with cancer express significantly reduced levels of the TNFR protein and mRNA encoding the TNFR when compared to a corresponding "standard" level. Further, it is believed that reduced levels of the TNFR protein can be detected in certain body fluids (e.g., sera and plasma) from mammals with such a cancer when compared to sera from mammals of the same species not having the cancer.

Thus, the invention provides a diagnostic method useful during diagnosis of an immune system disorder, including cancers which involves measuring the expression level of the gene encoding the TNFR protein in immune system tissue or other cells or body fluid from an individual and comparing the measured gene expression level with a standard TNFR gene expression level, whereby an increase or decrease in the gene expression level compared to the standard is indicative of an immune system disorder.

Where a diagnosis of a disorder in the immune system including diagnosis of a tumor has already been made according to conventional methods, the present invention is useful as a prognostic indicator, whereby patients exhibiting depressed gene expression will experience a worse clinical outcome relative to patients expressing the gene at a level nearer the standard level.

By "assaying the expression level of the gene encoding a TNFR protein" is intended qualitatively or quantitatively measuring or estimating the level of the TNFR-6α and/or -6β protein or the level of the mRNA encoding the TNFR-6α and/or -6β protein in a first biological sample either directly (e.g., by determining or estimating absolute protein level or mRNA level) or relatively (e.g., by comparing to the TNFR protein level or mRNA level in a second biological sample). Preferably, the TNFR protein level or mRNA level in the first biological sample is measured or estimated and compared to a standard TNFR protein level or mRNA level, the standard being taken from a second biological sample obtained from an individual not having the disorder or being determined by averaging levels from a population of individuals not having a disorder of the immune system. As will be appreciated in the art, once standard TNFR protein levels or mRNA levels are known, they can be used repeatedly as a standard for comparison.

By "biological sample" is intended any biological sample obtained from an individual, body fluid, cell line, tissue culture, or other source which contains TNFR protein or mRNA. As indicated, biological samples include body fluids (such as sera, plasma, urine, synovial fluid and spinal fluid) which contain free extracellular domain(s) (or soluable form(s)) of a TNFR protein, immune system tissue, and other tissue sources found to express complete or extracellular domain of a TNFR. Methods for obtaining tissue biopsies and body fluids from mammals are well known in the art. Where the biological sample is to include mRNA, a tissue biopsy is the preferred source.

The invention also contemplates the use of a gene of the present invention for diagnosing mutations in a TNFR gene. For example, if a mutation is present in one of the genes of the present invention, conditions would result from a lack of production of the receptor polypeptides of the present invention. Further, mutations which enhance receptor polypeptide activity would lead to diseases associated with an over expression of the receptor polypeptide, e.g., endotoxic shock. Mutations in the genes can be detected by comparing the sequence of the defective gene with that of a normal one. Subsequently one can verify that a mutant gene is associated with a disease condition or the susceptibility to a disease condition. That is, a mutant gene which leads to the underexpression of the receptor polypeptides of the present invention would be associated with an inability of TNF to inhibit tumor growth.

Other immune system disorders which may be diagnosed by the foregoing assays include hypersensitivity, allergy, infectious disease, graft-host disease, immunodeficiency, autoimmune diseases and the like.

Individuals carrying mutations in the genes of the present invention may be detected at the DNA level by a variety of techniques. Nucleic acids used for diagnosis may be obtained from a patient's cells, such as from blood, urine, saliva and tissue biopsy among other tissues. The genomic DNA may be used directly for detection or may be amplified enzymatically by using PCR (Saiki et al., Nature, 324:163-166 (1986)) prior to analysis. RNA or cDNA may also be used for the same purpose. As an example, PCR primers complementary to the nucleic acid of the instant invention can be used to identify and analyze mutations in the human genes of the present invention. For example, deletions and insertions can be detected by a change in the size of the amplified product in comparison to the normal genotype. Point mutations can be identified by hybridizing amplified DNA to radiolabeled RNA or alternatively, radiolabeled antisense DNA sequences of the present invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequencing primary used with double stranded PCR product or a single stranded template molecule generated by a modified PCR product. The sequence determination is performed by conventional procedures with radiolabeled nucleotides or by automatic sequencing procedures with fluorescent tags.

Sequence changes at the specific locations may be revealed by nuclease protection assays, such as RNase and S1 protection or the chemical cleavage method (for example, Cotton et al., PNAS, 85:4397-4401 (1985)).

Assaying TNFR protein levels in a biological sample can occur using antibody-based techniques. For example, TNFR protein expression in tissues can be studied with classical immunohistological methods (Jalkanen, M., et al., J. Cell. Biol. 101:976-985 (1985); Jalkanen, M., et al., J. Cell. Biol. 105:3087-3096 (1987)). Other antibody-based methods useful for detecting TNFR gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{2}$In), and technetium ($^{99m}$Tc), and fluorescent labels, such as fluorescein and rhodamine, and biotin.

In addition to assaying TNFR protein levels in a biological sample obtained from an individual, TNFR proteins can also be detected in vivo by imaging. Antibody labels or markers for in vivo imaging of TNFR proteins include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A TNFR-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain TNFR protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Treatment

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," *Symp. Quant. Biol.* 51:597-609 (1986), Cold Spring Harbor; Beutler, B., and Cerami, A., *Annu. Rev. Biochem.* 57:505-518 (1988); Old, L. J., *Sci. Am.* 258:59-75 (1988); Fiers, W., *FEBS Lett.* 285:199-224 (1991)). The TNF-family ligands induce such various cellular responses by binding to TNF-family receptors. Cells which express a TNFR polypeptide and have a potent cellular response to TNFR-6α and -6β ligands include lymphocytes, endothelial cells, keratinocytes, and prostate tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis.

Diseases associated with increased cell survival, or the inhibition of apoptosis, include cancers (such as follicular lymphomas, carcinomas with p53 mutations, and hormone-dependent tumors, such as breast cancer, prostate cancer, Kaposi's sarcoma and ovarian cancer); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Thus, in one aspect, the present invention is directed to a method for enhancing apoptosis induced by a TNF-family ligand, which involves administering to a cell which expresses the TNFR polypeptide an effective amount of TNFR polypeptide, analog or an agonist capable of increasing TNFR mediated signaling. Preferably, TNFR mediated signaling is increased to treat a disease wherein decreased apoptosis is exhibited. Antagonist can include soluble forms of TNFR and monoclonal antibodies directed against the TNFR polypeptide.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246: 181-296 (October 1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique involves expressing in cells a construct wherein the receptor is linked to a phospholipase C or D. Such cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Further screening assays for agonist and antagonist of the present invention are described in Tartaglia, L. A., and Goeddel, D. V., *J. Biol. Chem.* 267(7):4304-4307 (1992).

Thus, in a further aspect, a screening method is provided for determining whether a candidate agonist or antagonist is capable of enhancing or inhibiting a cellular response to a TNF-family ligand. The method involves contacting cells which express the TNFR polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TNFR polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonist include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457-1458 (1995)). Further preferred agonist include polyclonal and monoclonal antibodies raised against the TNFR polypeptide, or a fragment thereof. Such agonist antibodies raised against a TNF-family receptor are disclosed in Tartaglia, L. A., et al., *Proc. Natl. Acad. Sci. USA* 88:9292-9296 (1991); and Tartaglia, L. A., and Goeddel, D. V., *J. Biol. Chem.* 267 (7):4304-4307 (1992) See, also, PCT Application WO 94/09137.

Antagonist according to the present invention include naturally occurring and synthetic compounds such as, for example, the CD40 ligand, neutral amino acids, zinc, estrogen, androgens, viral genes (such as Adenovirus EIB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and -Hexachlorocyclohexane). Other antagonists include polyclonal and monoclonal antagonist antibodies raised against the TNFR polypeptides or a fragment thereof. Such antagonist antibodies raised against a TNF-family receptor are described in Tartaglia, L. A., and Goeddel, D. V., *J. Biol. Chem.* 267(7):4304-4307 (1992) and Tartaglia, L. A. et al., *Cell* 73:213-216 (1993). See, also, PCT Application WO 94/09137.

Other potential antagonists include antisense molecules. Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. The oligonucleotides described above can also be delivered to cells such that the antisense RNA or DNA may be expressed in vivo to inhibit production of the receptor.

Further antagonist according to the present invention include soluble forms of TNFR, i.e., TNFR fragments that include the ligand binding domain from the extracellular region of the full length receptor. Such soluble forms of the receptor, which may be naturally occurring or synthetic, antagonize TNFR mediated signaling by competing with the cell surface TNFR for binding to TNF-family ligands. Thus, soluble forms of the receptor that include the ligand binding domain are novel cytokines capable of inhibiting tumor necrosis induced by TNF-family ligands. Other such cytokines are known in the art and include Fas B (a soluble form of the mouse Fas receptor) that acts physiologically to limit apoptosis induced by Fas ligand (Hughes, D. P. and Crispe, I. N., *J. Exp. Med.* 182:1395-1401 (1995)).

As indicated polyclonal and monoclonal antibody agonist or antagonist according to the present invention can be raised according to the methods disclosed in Tartaglia, L. A., and Goeddel, D. V., *J. Biol. Chem.* 267(7):4304-4307 (1992); Tartaglia, L. A. et al., *Cell* 73:213-216 (1993), and PCT Application WO 94/09137. The term "antibody" (Ab) or "monoclonal antibody" (mAb) as used herein is meant to include intact molecules as well as fragments thereof (such as, for example, Fab and F(ab')$_2$ fragments) which are capable of binding an antigen. Fab and F (ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of methods described above, and known in the art Proteins and other compounds which bind the extracellular domains are also candidate agonist and antagonist according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, J. et al., *Cell* 75:791-803 (1993); Zervos, A. S. et al., *Cell* 72:223-232 (1993)).

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to, the TNFR-6α & -6β ligands, TNF-α, lymphdtoxin-α (LT-α, also known as TNF-β), LT-β, FasL, CD40, CD27, CD30, 4-1BB, OX40, TRAIL and nerve growth factor (NGF).

Representative therapeutic applications of the present invention are discussed in-more detail below. The state of immunodeficiency that defines AIDS is secondary to a decrease in the number and function of CD4$^+$ T-lymphocytes. Recent reports estimate the daily loss of CD4$^+$ T cells to be between 3.5×107 and 2×109 cells (Wei X., et al., Nature 373:117-122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., *AIDS* 8:1197-1213 (1994); Finkel, T. H., and Banda, N. K., *Curr. Opin. Immunol.* 6:605-615 (1995); Muro-Cacho, C. A. et al., *J. Immunol.* 154:5555-5566 (1995)). Furthermore, apoptosis and CD4$^+$ T-lymphocyte depletion is tightly correlated in different animal models of AIDS (Brunner, T., et al., *Nature* 373:441-444 (1995); Gougeon, M. L., et al., *AIDS Res. Hum. Retroviruses* 9:553-563 (1993)) and, apoptosis is not observed in those animal models in which viral replication does not result in AIDS (Gougeon, M. L. et al., *AIDS Res. Hum. Retroviruses* 9:553-563 (1993)). Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley, A. D. et al., *J. Virol.* 70:199-206 (1996)). Further the TNF-family ligand was detectable in uninfected macrophages and its expression was upregulated following HIV infection resulting in selective killing of uninfected CD4 T-lymphocytes (Badley, A. D et al., *J. Virol.* 70:199-206 (1996)). Thus, by the invention, a method for treating HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way that, for example, viruses and bacteria have been presented. In the case of allograft rejection, immunosuppressive regimens are designed to prevent the immune system from reaching the effector stage. However, the immune profile of xenograft rejection may resemble disease recurrence more that allograft rejection. In the case of disease recurrence, the immune system has already been activated, as evidenced by destruction of the native islet cells. Therefore, in disease recurrence the immune system is already at the effector stage. Agonist of the present invention are able to suppress the immune response to both allografts and xenografts because lymphocytes activated and differentiated into effector cells will express the TNFR polypeptide, and thereby are susceptible to compounds which enhance TNFR activity. Thus, the present invention further provides a method for creating immune privileged tissues. Antagonist of the invention can further be used in the treatment of Inflammatory Bowel-Disease.

Formulations

The TNFR polypeptide composition will be formulated and dosed in a fashion consistent with good medical practice, taking into account the clinical condition of the individual patient (especially the side effects of treatment with TNFR-6α or -6β polypeptide alone), the site of delivery of the TNFR polypeptide composition, the method of administration, the scheduling of administration, and other factors known to practitioners. The "effective amount" of TNFR polypeptide for purposes herein is thus determined by such considerations.

As a general proposition, the total pharmaceutically effective amount of TNFR polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TNFR polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the TNFR of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, infrasternal, subcutaneous and intraarticular injection and infusion.

The TNFR polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly (2-hydroxyethyl methacrylate) (R. Langer et al., *J. Biomed. Mater. Res.* 15:167-277 (1981), and R. Langer, *Chem. Tech.* 12:98-105 (1982)), ethylene vinyl acetate (R. Langer et al., Id.) or poly-D-(−)-3-hydroxybutyric acid (EP 133,988). Sustained-release TNFR polypeptide compositions also include liposomally entrapped TNFR polypeptides. Liposomes containing TNFR polypeptides are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal TNFR polypeptide therapy.

For parenteral administration, in one embodiment, the TNFR polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the TNFR polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The TNFR polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of TNFR polypeptide salts.

TNFR polypeptides to be used for therapeutic administration must be sterile. Sterility is readily accomplished by filtration through sterile filtration membranes (e.g., 0.2 micron membranes). Therapeutic TNFR polypeptide compositions generally are placed into a container having a sterile access port, for example, an intravenous solution bag or vial having a stopper pierceable by a hypodermic injection needle.

TNFR polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous TNFR polypeptide solution, and the resulting mixture is lyophilized. The infusion solution is prepared by reconstituting the lyophilized TNFR polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNAs herein disclosed are used to clone genomic DNA of a TNFR protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of TNFR-6α and -6β in *E. coli*

The bacterial expression vector pQE60 is used for bacterial expression in this example (QIAGEN, Inc., 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such a way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequences encoding the desired portions of TNFR-6α and -6β proteins comprising the mature forms of the TNFR-6α and -6β amino acid sequences are amplified from the deposited cDNA clones using PCR oligonucleotide primers which anneal to the amino terminal sequences of the desired portions of the TNFR-6α or -6β proteins and to sequences in the deposited constructs 3' to the cDNA coding sequence. Additional nucleotides containing restriction sites to facilitate cloning in the pQE60 vector are added to the 5' and 3' sequences, respectively.

For cloning the mature form of the TNFR-6α protein, the 5' primer has the sequence 5' CGC CCATGGCAGAAACACCCACCTAC 3' (SEQ ID NO:19) containing the underlined NcoI restriction site. One of ordinary skill in the art would appreciate, of course, that the point in the protein coding sequence where the 5' primer begins may be varied to amplify a desired portion of the complete protein shorter or longer than the mature form. The 3' primer has the sequence 5' CGC AAGCTTCTCTTTCAGTGCAAGTG 3' (SEQ ID NO:20) containing the underlined HindIII restriction site. For cloning the mature form of the TNFR-6β protein, the 5' primer has the sequence of SEQ ID NO:19 above, and the 3' primer has the sequence 5'CGCAAGCTTCTCCTCAGCTCCTGCAGTG 3' (SEQ ID NO:21) containing the underlined HindIII restriction site.

The amplified TNFR-6α and -6β DNA fragments and the vector pQE60 are digested with NcoI and HindIII and the digested DNAs are then ligated together. Insertion of the TNFR-6α and -6β DNA into the restricted pQE60 vector places the TNFR-6α and -6β°protein coding region including its associated stop codon downstream from the IPTG-inducible promoter and in-frame with an initiating AUG. The associated stop codon prevents translation of the six histidine codons downstream of the insertion point. The ligation mixture is transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing TNFR-6α or -6β protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-b-D-thiogalactopyranoside ("IPTG") is then added to a final concentration of 1 mM to induce transcription from the lac repressor sensitive promoter, by inactivating the lad repressor. Cells subsequently are incubated further for 3 to 4 hours. Cells then are harvested by centrifugation.

To purify the TNFR-6α and -6β polypeptide, the cells are then stirred for 3-4 hours at 4° C. in 6M guanidine-HCl, pH 8. The cell debris is removed by centrifugation, and the supernatant containing the TNFR-6α and -6β is dialyzed against 50 mM Na-acetate buffer pH 6, supplemented with 200 mM NaCl. Alternatively, the protein can be successfully refolded by dialyzing it against 500 mM NaCl, 20% glycerol, 25 mM Tris/HCl pH 7.4, containing protease inhibitors. After renaturation the protein can be purified by ion exchange, hydrophobic interaction and size exclusion chromatography. Alternatively, an affinity chromatography step such as an antibody column can be used to obtain pure TNFR-6α and -6β protein. The purified protein is stored at 4° C. or frozen at −80° C.

The following alternative method may be used to purify TNFR-6α or -6β expressed in *E. coli* when it is present in the form of inclusion bodies. Unless otherwise specified, all of the following steps are conducted at 4-10° C. Upon completion of the production phase of the *E. coli* fermentation, the cell culture is cooled to 4-10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the TNFR-6α or -6β polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded TNF receptor polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the TNF receptor polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the TNFR-6α or -6β polypeptide (determined, for instance, by 16% SDS-PAGE) are then pooled.

The resultant TNF receptor polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of TNFR-6α and -6β Proteins in a Baculovirus Expression System In this illustrative example, the plasmid shuttle vector pA2 is used to insert the cloned DNA encoding complete protein, including its naturally associated secretory signal (leader) sequence, into a baculovirus to express the mature TNFR-6α or -6β protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa califormica* nuclear polyhedrosis virus (AcMNPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the full length TNFR-6α or -6β protein in a deposited clone, including the AUG initiation codon and the naturally associated leader sequence shown in SEQ ID NO:2 or 4 is amplified using PCR oligonucleotide primers corresponding to the 5' and 3' sequences of the gene. The 5' primer for TNFR-6α and -6β has the sequence 5' CGC GGATCCGCCATCATGAGGGCGTGGAGGGGCCAG 3' (SEQ ID NO:22) containing the underlined BamHI restriction enzyme site. All of the previously described primers encode an efficient signal for initiation of translation in eukaryotic cells, as described by Kozak, M., *J. Mol. Biol.* 196:947-950 (1987). The 3' primer for TNFR-6α has the sequence a 5' CGCGGTACCCTCTTTCAGTGCAAGTG 3' (SEQ ID NO: 23) containing the underlined Asp718 restriction site. The 3' primer for TNFR-6β has the sequence 5' CGC GGTACCCTCCTCAGCTCCTGCAGTG 3' (SEQ ID NO:24) containing the underlined Asp718 restriction site.

The amplified fragment is isolated from a 1% agarose gel using a commercially available kit ("Geneclean," BIO 101 Inc., La Jolla, Calif.). The fragment then is digested with the appropriate restriction enzyme for each of the primers used, as specified above, and again is purified on a 1% agarose gel.

The plasmid is digested with the same restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and dephosphorylated plasmid are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human TNF receptor gene by digesting DNA from individual colonies using the enzymes used immediately above and then analyzing the digestion product by gel electrophoresis. The sequence of the cloned fragment is confirmed by DNA sequencing. This plasmid is designated herein pA2-TNFR-6α or pA2TNFR-6β (collectively pA2-TNFR).

Five μg of the plasmid pA2-TNFR is co-transfected with 1.0 μg of a commercially available linearized baculovirus DNA ("BaculoGold™ baculovirus DNA", Pharmingen, San Diego, Calif.), using the lipofection method described by Feigner et al., *Proc. Natl. Acad. Sci. USA* 84: 7413-7417 (1987). One μg of BaculoGold™ virus DNA and 5 μg of the plasmid pA2-TNFR are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C.

To verify the expression of the TNF receptor gene Sf9 cells are grown in Grace's medium supplemented with 10% heat-inactivated FBS. The cells are infected with the recombinant baculovirus at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 of $^{35}$S-methionine and 5 μCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the mature form of the TNF receptor protein.

Example 3

Cloning and Expression of TNFR-6α and -6$ in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10:169-175

(1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology,* 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTNFR-α-HA and -6β-HA, is made by cloning a portion of the cDNA encoding the mature form of the TNF receptor protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37: 767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the complete TNF receptor polypeptide is cloned into the polylinker region of the vector so that recombinant protein expression is directed by the CMV promoter. The plasmid construction strategy is as follows. The TNF receptor cDNA of a deposited clone is amplified using primers that contain convenient restriction sites, much as described above for construction of vectors for expression of a TNF receptor in *E. coli*. Suitable primers can easily be designed by those of ordinary skill in the art.

The PCR amplified DNA fragment and the vector, pcDNAI/Amp, are digested with XbaI and EcoRI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the TNFR-α and -6β polypeptides.

For expression of recombinant TNFR-α and -6β, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TNFR by the vector.

Expression of the pTNFR-α-HA and -6β-HA fusion protein is detected by radiolabeling and immunoprecipitation, using methods described in, for example Harlow et al., *Antibodies: A Laboratory Manual, 2nd Ed.*; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TNFR-6α and -6β polypeptides. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438-447) plus a fragment isolated from the enhancer of the immediate early gene of human cytomegalovirus (CMV) (Boshart et al., *Cell* 41:521-530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TNF receptor polypeptide in a regulated way in mammalian cells (Gossen, M., & Bujard, H.1992, *Proc. Natl. Acad. Sci. USA* 89:5547-

5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes appropriate for the specific primers used to amplify the TNF receptor of choice as outlined below and then dephosphorylated using calf intestinal phosphates by procedures known in the art. The vector is then isolated from a 1% agarose gel.

The DNA sequence encoding the TNF receptor polypeptide is amplified using PCR oligonucleotide primers corresponding to the 5' and 3' sequences of the desired portion of the gene. The 5' primer for TNFR-6α and -6β containing the underlined BamHI site, has the following sequence: 5' CGC GGATCCGCCATCATGAGGGCGTGGAGGGGCCAG 3' (SEQ ID NO: 22). The 3' primer for TNFR-6α has the sequence 5' CGCGGTACCCTCTTTCAGTGCAAGTG 3' (SEQ ID NO: 23) containing the underlined Asp718 restriction site. The 3' primer for TNFR-6β has the sequence 5' CGC GGTACCCTCCTCAGCTCCTGCAGTG 3' (SEQ ID NO: 24) containing the underlined Asp718 restriction site.

The amplified fragment is digested with the endonucleases which will cut at the engineered restriction site(s) and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSVneo using lipofectin (Feigner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100-200 μM. Expression of the desired gene product is analyzed, for instance, by SDS-PAGE and Western blot or by reversed phase HPLC analysis.

Example 4

Tissue Distribution of TNF Receptor mRNA Expression

Northern blot analysis is carried out to examine TNFR-6α or -6β gene expression in human tissues, using methods described by, among others, Sambrook et al., cited above. A cDNA probe containing the entire nucleotide sequence of a TNF receptor protein (SEQ ID NO:1 or 3) is labeled with $^{32}$P using the Rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for TNF receptor mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated nucleic acid molecule comprising a nucleotide sequence selected from the group consisting of:

(a) a nucleotide sequence encoding amino acid residues 1 to 300 of SEQ ID NO:2;

(b) a nucleotide sequence encoding amino acid residues 2 to 300 of SEQ ID NO:2;

(c) a nucleotide sequence encoding amino acid residues 31 to 300 of SEQ ID NO:2;

(d) a nucleotide sequence encoding amino acid residues 31 to 283 of SEQ ID NO:2; and (e) a nucleotide sequence that is the complement of (a), (b), (c), or (d).

2. The nucleic acid molecule of claim 1 comprising a nucleotide sequence according to (a).

3. The nucleic acid molecule of claim 2 comprising nucleotides 25 to 924 of SEQ ID NO:1.

4. The nucleic acid molecule of claim 1 comprising a nucleotide sequence according to (b).

5. The nucleic acid molecule of claim 1 comprising a nucleotide sequence according to (c).

6. The nucleic acid molecule of claim 1 comprising a nucleotide sequence according to (d).

7. The nucleic acid molecule of claim 1 comprising a nucleotide sequence according to (e).

8. The nucleic acid molecule of claim 1 further comprising a nucleotide sequence heterologous to SEQ ID NO:1.

9. The nucleic acid molecule of claim 8, wherein said heterologous nucleotide sequence encodes a polypeptide heterologous to SEQ ID NO:2.

10. The nucleic acid molecule of claim 9, wherein said heterologous polypeptide is an Fc domain of immunoglobulin.

11. A recombinant vector comprising the nucleic acid molecule of claim 1.

12. The recombinant vector of claim 11, wherein the nucleic acid molecule is operably associated with a regulatory element that controls expression of said nucleic acid molecule.

13. An isolated recombinant host cell comprising the vector of claim 11.

14. An isolated host cell comprising the nucleic acid molecule of claim 1 operably associated with a regulatory element that controls expression of said nucleic acid molecule.

15. A method of producing a polypeptide encoded by the nucleic acid molecule of claim 1(a)-(d), comprising:
   (a) culturing a host cell comprising said nucleic acid molecule under conditions suitable to produce said polypeptide; and
   (b) recovering said polypeptide from the culture.

16. A composition comprising the nucleic acid molecule of claim 1 and a pharmaceutically acceptable carrier.

17. An isolated nucleic acid molecule comprising a nucleotide sequence encoding a first amino acid sequence at least 90% identical to the entire length of a second amino acid sequence selected from the group consisting of:
   (a) amino acid residues 1 to 300 of SEQ ID NO:2;
   (b) amino acid residues 2 to 300 of SEQ ID NO:2;
   (c) amino acid residues 31 to 300 of SEQ ID NO:2; and
   (d) amino acid residues 31 to 283 of SEQ ID NO:2;
wherein a protein consisting of said first amino acid sequence binds Fas ligand.

18. The nucleic acid molecule of claim 17 encoding a first amino acid sequence at least 90% identical to a second amino acid sequence according to (a).

19. The nucleic acid molecule of claim 17 encoding a first amino acid sequence at least 90% identical to an amino acid sequence according to (b).

20. The nucleic acid molecule of claim 17 encoding a first amino acid sequence at least 90% identical to a second amino acid sequence according to (c).

21. The nucleic acid molecule of claim 17 encoding a first amino acid sequence at least 90% identical to a second amino acid sequence according to (d).

22. The nucleic acid molecule of claim 21 encoding a first amino acid sequence at least 95% identical to a second amino acid sequence according to (d).

23. The nucleic acid molecule of claim 21 that further comprises a nucleotide sequence heterologous to SEQ ID NO:1.

24. The nucleic acid molecule of claim 23, wherein said heterologous nucleotide sequence encodes a polypeptide heterologous to SEQ ID NO:2.

25. The nucleic acid molecule of claim 24, wherein said heterologous polypeptide is an Fc domain of immunoglobulin.

26. A recombinant vector comprising the nucleic acid molecule of claim 21.

27. The recombinant vector of claim 26, wherein the nucleic acid molecule is operably associated with a regulatory element that controls expression of said nucleic acid molecule.

28. An isolated host cell comprising the vector of claim 26.

29. An isolated host cell comprising the nucleic acid molecule of claim 21 operably associated with a regulatory element that controls expression of said nucleic acid molecule.

30. A method of producing a polypeptide encoded by the nucleic acid molecule of claim 21 comprising:
   (a) culturing a host cell comprising said nucleic acid molecule under conditions suitable to produce said polypeptide; and
   (b) recovering said polypeptide from the culture.

31. A composition comprising the nucleic acid molecule of claim 21 and a pharmaceutically acceptable carrier.

32. An isolated nucleic acid molecule comprising the complement of the nucleotide sequence of claim 17.

33. An isolated nucleic acid molecule comprising a nucleotide sequence selected from the group consisting of:
   (a) a nucleotide sequence encoding the full-length polypeptide encoded by the cDNA contained in clone HPHAE52 as deposited with the ATCC as accession number 97810;
   (b) a nucleotide sequence encoding the full-length polypeptide, lacking the N-terminal methionine, which is encoded by the cDNA contained in clone HPHAE52 as deposited with the ATCC as accession number 97810;
   (c) a nucleotide sequence encoding the mature polypeptide encoded by the cDNA contained in clone HPHAE52 as deposited with the ATCC as accession number 97810;
   (d) a nucleotide sequence encoding the soluble extracellular domain encoded by the cDNA contained in clone HPHAE52 as deposited with the ATCC as accession number 97810, respectively; and
   (e) a nucleotide sequence that is the complement of (a), (b), (c), or (d).

34. The nucleic acid molecule of claim 33 comprising a nucleotide sequence according to (a).

35. The nucleic acid molecule of claim 33 comprising a nucleotide sequence according to (b).

36. The nucleic acid molecule of claim 33 comprising a nucleotide sequence according to (c).

37. The nucleic acid molecule of claim 36 comprising the nucleotide sequence of the cDNA that encodes the mature polypeptide encoded by clone HPHAE52, which clone was deposited with the ATCC as accession number 97810.

38. The nucleic acid molecule of claim 36 further comprising a nucleotide sequence heterologous to the cDNA contained in clone HPHAE52 as deposited with the ATCC as accession number 97810.

39. The nucleic acid molecule of claim 38, wherein said heterologous nucleotide sequence encodes a polypeptide heterologous to the polypeptide encoded by the cDNA contained in clone HPHAE52, which clone was deposited with the ATCC as accession number 97810.

40. The nucleic acid molecule of claim 39, wherein said heterologous polypeptide is an Fc domain of immunoglobulin.

41. A recombinant vector comprising the nucleic acid molecule of claim 36.

42. The recombinant vector of claim 41, wherein the nucleic acid molecule is operably associated with a regulatory element that controls expression of said nucleic acid molecule.

43. An isolated host cell comprising the vector of claim 41.

44. An isolated host cell comprising the nucleic acid molecule of claim 36 operably associated with a regulatory element that controls expression of said nucleic acid molecule.

45. A method of producing a polypeptide encoded by the nucleic acid molecule of claim 36, comprising:
(a) culturing a host cell comprising said nucleic acid molecule under conditions suitable to produce said polypeptide; and
(b) recovering said polypeptide from the culture.

46. A composition comprising the nucleic acid molecule of claim 36 and a pharmaceutically acceptable carrier.

47. The nucleic acid molecule of claim 33 comprising a nucleotide sequence according to (d).

48. The nucleic acid molecule of claim 33 comprising a nucleotide sequence according to (e).

49. An isolated nucleic acid molecule comprising a nucleotide sequence encoding a first amino acid sequence at least 90% identical to the entire length of a second amino acid sequence selected from the group consisting of:
(a) the amino acid sequence of the full-length polypeptide encoded by the cDNA contained in clone HPHAE52 as deposited with the ATCC as accession number 97810;
(b) the amino acid sequence of the full-length polypeptide, lacking the N-terminal methionine, which is encoded by the cDNA contained in clone HPHAE52 as deposited with the ATCC as accession number 97810;
(c) the amino acid sequence of the mature polypeptide encoded by the cDNA contained in clone HPHAE52 as deposited with the ATCC as accession number 97810; and
(d) the amino acid sequence of the soluble extracellular domain of the polypeptide encoded by the cDNA contained in clone HPHAE52 as deposited with the ATCC as accession number 97810;
wherein a protein consisting of said first amino acid sequence binds Fas ligand.

50. The nucleic acid molecule of claim 49 encoding a first amino acid sequence at least 90% identical to a second amino acid sequence according to (a).

51. The nucleic acid molecule of claim 49 encoding a first amino acid sequence at least 90% identical to a second amino acid sequence according to (b).

52. The nucleic acid molecule of claim 49 encoding a first amino acid sequence at least 90% identical to a second amino acid sequence according to (c).

53. The nucleic acid molecule of claim 52 encoding a first amino acid sequence at least 95% identical to a second amino acid sequence according to (c).

54. The nucleic acid molecule of claim 52 that further comprises a nucleotide sequence heterologous to the cDNA contained in clone HPHAE52 as deposited with the ATCC as accession number 97810.

55. The nucleic acid molecule of claim 54, wherein said heterologous nucleotide sequence encodes a polypeptide heterologous to the polypeptide encoded by the cDNA contained in clone HPHAE52 as deposited with the ATCC as accession number 97810.

56. The nucleic acid molecule of claim 55, wherein said heterologous polypeptide is an Fc domain of immunoglobulin.

57. A recombinant vector comprising the nucleic acid molecule of claim 52.

58. The recombinant vector of claim 57, wherein the nucleic acid molecule is operably associated with a regulatory element that controls expression of said nucleic acid molecule.

59. An isolated host cell comprising the vector of claim 57.

60. An isolated host cell comprising the nucleic acid molecule of claim 52 operably associated with a regulatory element that controls expression of said nucleic acid molecule.

61. A method of producing a polypeptide encoded by the nucleic acid molecule of claim 52 comprising:
(a) culturing a host cell comprising said nucleic acid molecule under conditions suitable to produce said polypeptide; and
(b) recovering said polypeptide from the culture.

62. A composition comprising the nucleic acid molecule of 52 and a pharmaceutically acceptable carrier.

63. The nucleic acid molecule of claim 49 encoding a first amino acid sequence at least 90% identical to a second amino acid sequence according to (d).

64. An isolated nucleic acid molecule comprising the complement of the nucleotide sequence of claim 49.

65. An isolated nucleic acid molecule comprising a nucleotide sequence selected from the group consisting of:
(a) a nucleotide sequence encoding amino acid residues m-300 of SEQ ID NO:2, where m is an integer in the range of 1 to 49;
(b) a nucleotide sequence encoding amino acid residues 1-y of SEQ ID NO:2, where y is an integer in the range of 193 to 300;
(c) a nucleotide sequence encoding amino acid residues m-y of SEQ ID NO:2, where m is an integer in the range of 1 to 49 and y is an integer in the range of 193 to 300; and
(d) a nucleotide sequence that is the complement of (a), (b), or (c);
wherein a protein consisting of said amino acid residues bind Fas ligand.

66. The nucleic acid molecule of claim 65 comprising a nucleotide sequence according to (a).

67. The nucleic acid molecule of claim 65 comprising a nucleotide sequence according to (b).

68. The nucleic acid molecule of claim 65 comprising a nucleotide sequence according to (c).

69. The nucleic acid molecule of claim 65 comprising a nucleotide sequence according to (d).

70. The nucleic acid molecule of claim 65 wherein the nucleotide sequence encodes amino acid residues 49 to 300 of SEQ ID NO:2.

71. The nucleic acid molecule of claim 65 wherein the nucleotide sequence encodes amino acid residues 1 to 193 of SEQ ID NO:2.

72. The nucleic acid molecule of claim 65 further comprising a nucleotide sequence heterologous to SEQ ID NO:1.

73. The nucleic acid molecule of claim 72, wherein said heterologous nucleotide sequence encodes a polypeptide heterologous to SEQ ID NO:2.

74. The nucleic acid molecule of claim 73, wherein said heterologous polypeptide is an Fc domain of immunoglobulin.

75. A recombinant vector comprising the nucleic acid molecule of claim 65.

76. The recombinant vector of claim 75, wherein the nucleic acid molecule is operably associated with a regulatory element that controls expression of said nucleic acid molecule.

77. An isolated host cell comprising the vector of claim 75.

78. An isolated host cell comprising the nucleic acid molecule of claim 65 operably associated with a regulatory element that controls expression of said nucleic acid molecule.

79. A method of producing a polypeptide encoded by the nucleic acid molecule of claim 65(a)-(c), comprising:
(a) culturing a host cell comprising said nucleic acid molecule under conditions suitable to produce said polypeptide; and
(b) recovering said polypeptide from the culture.

80. A composition comprising the nucleic acid molecule of claim 65 and a pharmaceutically acceptable carrier.

81. An isolated nucleic acid molecule comprising a nucleotide sequence selected from the group consisting of:
(a) a nucleotide sequence encoding a polypeptide comprising a portion of the complete amino acid sequence encoded by the cDNA clone contained in ATCC Deposit 97810 wherein said portion excludes up to 48 amino acids from the amino terminus of the complete amino acid sequence;
(b) a nucleotide sequence encoding a polypeptide comprising a portion of the complete amino acid sequence encoded by the cDNA clone contained in ATCC Deposit 97810 wherein said portion excludes up to 107 amino acids from the carboxy terminus of the complete amino acid sequence;
(c) a nucleotide sequence encoding a polypeptide comprising a portion of the complete amino acid sequence encoded by the cDNA clone contained in ATCC Deposit 97810 wherein said portion excludes up to 48 amino acids from the amino terminus and up to 107 amino acids from the carboxy terminus of the complete amino acid sequence; and
(d) a nucleotide sequence that is the complement of (a), (b), or (c);
wherein said polypeptide consisting of a portion of the complete amino acid sequence encoded by the cDNA clone contained in ATCC Deposit 97810 binds Fas ligand.

82. The nucleic acid molecule of claim 81 comprising a nucleotide sequence according to (a).

83. The nucleic acid molecule of claim 81 comprising a nucleotide sequence according to (b).

84. The nucleic acid molecule of claim 81 comprising a nucleotide sequence according to (c).

85. The nucleic acid molecule of claim 81 comprising a nucleotide sequence according to (d).

86. The nucleic acid molecule of claim 81 further comprising a nucleotide sequence heterologous to said cDNA clone.

87. The nucleic acid molecule of claim 86, wherein said heterologous nucleotide sequence encodes a polypeptide heterologous to the polypeptide encoded by said cDNA clone.

88. The nucleic acid molecule of claim 87, wherein said heterologous polypeptide is an Fc domain of immunoglobulin.

89. A recombinant vector comprising the nucleic acid molecule of claim 81.

90. The recombinant vector of claim 89, wherein the nucleic acid molecule is operably associated with a regulatory element that controls expression of said nucleic acid molecule.

91. An isolated host cell comprising the vector of claim 89.

92. An isolated host cell comprising the nucleic acid molecule of claim 81 operably associated with a regulatory element that controls expression of said nucleic acid molecule.

93. A method of producing a polypeptide encoded by the nucleic acid molecule of claim 81(a)-(c), comprising:
(a) culturing a host cell comprising said nucleic acid molecule under conditions suitable to produce said polypeptide; and
(b) recovering said polypeptide from the culture.

94. A composition comprising the nucleic acid molecule of claim 81 and a pharmaceutically acceptable carrier.

95. An isolated polynucleotide comprising a polynucleotide of SEQ ID NO:1.

96. An isolated polynucleotide which is complementary to the polynucleotide of claim 95.

97. The isolated polynucleotide of SEQ ID NO:1.

98. An isolated polynucleotide which is complementary to the polynucleotide of claim 97.

99. An isolated polynucleotide comprising a nucleotide sequence that is at least 95% identical to a nucleotide sequence encoding amino acid residues 31-300 of SEQ ID NO:2 wherein said polynucleotide encodes a polypeptide that binds Fas ligand.

100. An isolated polynucleotide comprising a nucleotide sequence that is at least 95% identical to a nucleotide sequence encoding amino acid residues 31-283 of SEQ ID NO: 2 wherein said polynucleotide encodes a polypeptide that binds Fas ligand.

101. An expression vector for the production of a polypeptide comprising amino acids 31-300 of SEQ ID NO:2 comprising a polynucleotide that encodes amino acids 31-300 of SEQ ID NO:2 operably associated with a regulatory element that controls expression of said polynucleotide.

102. An isolated host cell comprising the expression vector of claim 101.

103. A process for producing an isolated host cell which produces a polypeptide comprising amino acids 31-300 of SEQ ID NO:2, comprising transforming or transfecting a host cell with the expression vector of claim 101 such that the host cell, under appropriate culture conditions, produces said polypeptide.

104. A method of for producing a polypeptide comprising amino acids 31-300 of SEQ ID NO:2, comprising culturing the host cell of claim 102 under conditions sufficient for the production of said polypeptide and recovering said polypeptide from the culture.

* * * * *

UNITED STATES PATENT AND TRADEMARK OFFICE
CERTIFICATE OF CORRECTION

| | | |
|---|---|---|
| PATENT NO. | : 8,003,386 B1 | Page 1 of 1 |
| APPLICATION NO. | : 09/006352 | |
| DATED | : August 23, 2011 | |
| INVENTOR(S) | : Gentz et al. | |

It is certified that error appears in the above-identified patent and that said Letters Patent is hereby corrected as shown below:

On the Title Page, item 57:

In the Abstract, line 1, delete "Necorsis" and insert -- Necrosis --.

In the Specification:

At column 6, line number 28, delete "2$\alpha$-B" and insert -- 2A-B --.

In the Claims:

At column 79, claim 13, line 26, delete "recombinant".

At column 84, claim 104, line 49, delete "A method of for producing" and insert -- A method of producing --.

Signed and Sealed this
Twenty-fifth Day of October, 2011

David J. Kappos
*Director of the United States Patent and Trademark Office*

SEQUENCE LISTING

```
<160> NUMBER OF SEQ ID NOS:  24

<210> SEQ ID NO 1
<211> LENGTH: 1077
<212> TYPE: DNA
<213> ORGANISM: Homo sapiens
<220> FEATURE:
<221> NAME/KEY: CDS
<222> LOCATION: (25)..(924)

<400> SEQUENCE: 1
gctctccctg ctccagcaag gacc atg agg gcg ctg gag ggg cca ggc ctg        51
                          Met Arg Ala Leu Glu Gly Pro Gly Leu
                            1               5 tcg ctg ctg tgc ctg gtg ttg gcg ctg cct gcc ctg ctg ccg gtg ccg        99
Ser Leu Leu Cys Leu Val Leu Ala Leu Pro Ala Leu Leu Pro Val Pro
 10              15                  20                  25
```

```
gct gta cgc gga gtg gca gaa aca ccc acc tac ccc tgg cgg gac gca      147
Ala Val Arg Gly Val Ala Glu Thr Pro Thr Tyr Pro Trp Arg Asp Ala
         30                  35                  40 gag aca ggg gag cgg ctg gtg tgc gcc cag tgc ccc cca ggc acc ttt      195
Glu Thr Gly Glu Arg Leu Val Cys Ala Gln Cys Pro Pro Gly Thr Phe
     45                  50                  55 gtg cag cgg ccg tgc cgc cga gac agc ccc acg acg tgt ggc ccg tgt      243
Val Gln Arg Pro Cys Arg Arg Asp Ser Pro Thr Thr Cys Gly Pro Cys
 60                  65                  70 cca ccg cgc cac tac acg cag ttc tgg aac tac ctg gag cgc tgc cgc      291
Pro Pro Arg His Tyr Thr Gln Phe Trp Asn Tyr Leu Glu Arg Cys Arg
             75                  80                  85 tac tgc aac gtc ctc tgc ggg gag cgt gag gag gag gca cgg gct tgc      339
Tyr Cys Asn Val Leu Cys Gly Glu Arg Glu Glu Glu Ala Arg Ala Cys
     90                  95                 100                 105 cac gcc acc cac aac cgt gcc tgc cgc tgc cgc acc ggc ttc ttc gcg      387
His Ala Thr His Asn Arg Ala Cys Arg Cys Arg Thr Gly Phe Phe Ala
                 110                 115                 120 cac gct ggt ttc tgc ttg gag cac gca tcg tgt cca cct ggt gcc ggc      435
His Ala Gly Phe Cys Leu Glu His Ala Ser Cys Pro Pro Gly Ala Gly
             125                 130                 135 gtg att gcc ccg ggc acc ccc agc cag aac acg cag tgc cag ccg tgc      483
Val Ile Ala Pro Gly Thr Pro Ser Gln Asn Thr Gln Cys Gln Pro Cys
         140                 145                 150 ccc cca ggc acc ttc tca gcc agc agc tcc agc tca gag cag tgc cag      531
Pro Pro Gly Thr Phe Ser Ala Ser Ser Ser Ser Glu Gln Cys Gln
     155                 160                 165 ccc cac cgc aac tgc acg gcc ctg ggc ctg gcc ctc aat gtg cca ggc      579
Pro His Arg Asn Cys Thr Ala Leu Gly Leu Ala Leu Asn Val Pro Gly
170                 175                 180                 185 tct tcc tcc cat gac acc ctg tgc acc agc tgc act ggc ttc ccc ctc      627
Ser Ser Ser His Asp Thr Leu Cys Thr Ser Cys Thr Gly Phe Pro Leu
                 190                 195                 200 agc acc agg gta cca gga gct gag gag tgt gag cgt gcc gtc atc gac      675
Ser Thr Arg Val Pro Gly Ala Glu Glu Cys Glu Arg Ala Val Ile Asp
             205                 210                 215 ttt gtg gct ttc cag gac atc tcc atc aag agg ctg cag cgg ctg ctg      723
Phe Val Ala Phe Gln Asp Ile Ser Ile Lys Arg Leu Gln Arg Leu Leu
         220                 225                 230 cag gcc ctc gag gcc ccg gag ggc tgg ggt ccg aca cca agg gcg ggc      771
Gln Ala Leu Glu Ala Pro Glu Gly Trp Gly Pro Thr Pro Arg Ala Gly
     235                 240                 245 cgc gcg gcc ttg cag ctg aag ctg cgt cgg cgg ctc acg gag ctc ctg      819
Arg Ala Ala Leu Gln Leu Lys Leu Arg Arg Arg Leu Thr Glu Leu Leu
250                 255                 260                 265 ggg gcg cag gac ggg gcg ctg ctg gtg cgg ctg ctg cag gcg ctg cgc      867
Gly Ala Gln Asp Gly Ala Leu Leu Val Arg Leu Leu Gln Ala Leu Arg
                 270                 275                 280 gtg gcc agg atg ccc ggg ctg gag cgg agc gtc cgt gag cgc ttc ctc      915
Val Ala Arg Met Pro Gly Leu Glu Arg Ser Val Arg Glu Arg Phe Leu
             285                 290                 295 cct gtg cac tgatcctggc cccctcttat ttattctaca tccttggcac              964
Pro Val His
         300 cccacttgca ctgaaagagg cttttttta aatagaagaa atgaggtttc ttaaagctta    1024 tttttataaa gctttttcat aaaaaaaaaa aaaaaaaaaa aaaaaaaaaa aaa          1077

<210> SEQ ID NO 2
<211> LENGTH: 300
<212> TYPE: PRT
```

<213> ORGANISM: Homo sapiens

<400> SEQUENCE: 2

```
Met Arg Ala Leu Glu Gly Pro Gly Leu Ser Leu Leu Cys Leu Val Leu
  1               5                  10                  15
Ala Leu Pro Ala Leu Leu Pro Val Pro Ala Val Arg Gly Val Ala Glu
              20                  25                  30
Thr Pro Thr Tyr Pro Trp Arg Asp Ala Glu Thr Gly Glu Arg Leu Val
         35                  40                  45
Cys Ala Gln Cys Pro Pro Gly Thr Phe Val Gln Arg Pro Cys Arg Arg
     50                  55                  60
Asp Ser Pro Thr Thr Cys Gly Pro Cys Pro Arg His Tyr Thr Gln
 65                  70                  75                  80
Phe Trp Asn Tyr Leu Glu Arg Cys Arg Tyr Cys Asn Val Leu Cys Gly
                 85                  90                  95
Glu Arg Glu Glu Glu Ala Arg Ala Cys His Ala Thr His Asn Arg Ala
            100                 105                 110
Cys Arg Cys Arg Thr Gly Phe Phe Ala His Ala Gly Phe Cys Leu Glu
        115                 120                 125
His Ala Ser Cys Pro Pro Gly Ala Gly Val Ile Ala Pro Gly Thr Pro
    130                 135                 140
Ser Gln Asn Thr Gln Cys Gln Pro Cys Pro Pro Gly Thr Phe Ser Ala
145                 150                 155                 160
Ser Ser Ser Ser Ser Glu Gln Cys Gln Pro His Arg Asn Cys Thr Ala
                165                 170                 175
Leu Gly Leu Ala Leu Asn Val Pro Gly Ser Ser Ser His Asp Thr Leu
            180                 185                 190
Cys Thr Ser Cys Thr Gly Phe Pro Leu Ser Thr Arg Val Pro Gly Ala
        195                 200                 205
Glu Glu Cys Glu Arg Ala Val Ile Asp Phe Val Ala Phe Gln Asp Ile
    210                 215                 220
Ser Ile Lys Arg Leu Gln Arg Leu Leu Gln Ala Leu Glu Ala Pro Glu
225                 230                 235                 240
Gly Trp Gly Pro Thr Pro Arg Ala Gly Arg Ala Ala Leu Gln Leu Lys
                245                 250                 255
Leu Arg Arg Arg Leu Thr Glu Leu Leu Gly Ala Gln Asp Gly Ala Leu
            260                 265                 270
Leu Val Arg Leu Leu Gln Ala Leu Arg Val Ala Arg Met Pro Gly Leu
        275                 280                 285
Glu Arg Ser Val Arg Glu Arg Phe Leu Pro Val His
    290                 295                 300
```

<210> SEQ ID NO 3
<211> LENGTH: 1667
<212> TYPE: DNA
<213> ORGANISM: Homo sapiens
<220> FEATURE:
<221> NAME/KEY: CDS
<222> LOCATION: (73)..(582)

<400> SEQUENCE: 3

```
tggcatgtcg gtcaggcaca gcagggtcct gtgtccgcgc tgagccgcgc tctccctgct    60
ccagcaagga cc atg agg gcg ctg gag ggg cca ggc ctg tcg ctg ctg tgc   111
              Met Arg Ala Leu Glu Gly Pro Gly Leu Ser Leu Leu Cys
                1               5                  10 ctg gtg ttg gcg ctg cct gcc ctg ctg ccg gtg ccg gct gta cgc gga    159
Leu Val Leu Ala Leu Pro Ala Leu Leu Pro Val Pro Ala Val Arg Gly
```

-continued

```
                15                  20                  25
gtg gca gaa aca ccc acc tac ccc tgg cgg gac gca gag aca ggg gag      207
Val Ala Glu Thr Pro Thr Tyr Pro Trp Arg Asp Ala Glu Thr Gly Glu
 30                  35                  40                  45 cgg ctg gtg tgc gcc cag tgc ccc cca ggc acc ttt gtg cag cgg ccg      255
Arg Leu Val Cys Ala Gln Cys Pro Pro Gly Thr Phe Val Gln Arg Pro
                 50                  55                  60 tgc cgc cga gac agc ccc acg acg tgt ggc ccg tgt cca ccg cgc cac      303
Cys Arg Arg Asp Ser Pro Thr Thr Cys Gly Pro Cys Pro Pro Arg His
             65                  70                  75 tac acg cag ttc tgg aac tac ctg gag cgc tgc cgc tac tgc aac gtc      351
Tyr Thr Gln Phe Trp Asn Tyr Leu Glu Arg Cys Arg Tyr Cys Asn Val
         80                  85                  90 ctc tgc ggg gag cgt gag gag gag gca cgg gct tgc cac gcc acc cac      399
Leu Cys Gly Glu Arg Glu Glu Glu Ala Arg Ala Cys His Ala Thr His
     95                 100                 105 aac cgt gcc tgc cgc tgc cgc acc ggc ttc ttc gcg cac gct ggt ttc      447
Asn Arg Ala Cys Arg Cys Arg Thr Gly Phe Phe Ala His Ala Gly Phe
110                 115                 120                 125 tgc ttg gag cac gca tcg tgt cca cct ggt gcc ggc gtg att gcc ccg      495
Cys Leu Glu His Ala Ser Cys Pro Pro Gly Ala Gly Val Ile Ala Pro
                130                 135                 140 ggt gag agc tgg gcg agg gga ggg gcc ccc agg agt ggt ggc cgg agg      543
Gly Glu Ser Trp Ala Arg Gly Gly Ala Pro Arg Ser Gly Gly Arg Arg
            145                 150                 155 tgt ggc agg ggt cag gtt gct ggt ccc agc ctt gca ccc tgagctagga      592
Cys Gly Arg Gly Gln Val Ala Gly Pro Ser Leu Ala Pro
        160                 165                 170 caccagttcc cctgaccctg ttcttccctc ctggctgcag gcaccccag ccagaacacg      652 cagtgccagc cgtgcccccc aggcaccttc tcagccagca gctccagctc agagcagtgc    712
cagccccacc gcaactgcac ggccctgggc ctggccctca atgtgccagg ctcttcctcc    772
catgacaccc tgtgcaccag ctgcactggc ttccccctca gcaccaggt accaggtgag     832 ccagaggcct gagggggcag cacactgcag gccaggccca cttgtgccct cactcctgcc    892
cctgcacgtg catctagcct gaggcatgcc agctggctct gggaaggggc acagtggat    952 ttgaggggtc aggggtccct ccactagatc cccaccaagt ctgccctctc aggggtggct    1012
gagaatttgg atctgagcca gggcacagcc tcccctggag agctctggga agtgggcag    1072 caatctccta actgcccgag gggaaggtgg ctggctcctc tgacacgggg aaaccgaggc    1132
ctgatggtaa ctctcctaac tgcctgagag aaggtggct gcctcctctg acatgggaa     1192 accgaggccc aatgttaacc actgttgaga agtcacaggg ggaagtgacc cccttaacat    1252
caagtcaggt ccgtccatc tgcaggtccc aactcgcccc ttccgatggc caggagccc     1312 caagcccttg cctgggcccc cttgcctctt gcagccaagg tccgagtggc cgctcctgcc    1372
ccctaggcct ttgctccagc tctctgaccg aaggctcctg ccccttctcc agtcccatc    1432 gttgcactgc cctctccagc acggctcact gcacagggat ttctctctcc tgcaaacccc    1492
ccgagtgggg cccagaaagc agggtacctg gcagcccccg ccagtgtgtg tgggtgaaat    1552
gatcggaccg ctgcctcccc acccactgc aggagctgag gagtgtgagc gtgccgtcat    1612
cgactttgtg gctttccagg acatctccat caagaggagc ggctgctgca ggccc         1667
```

<210> SEQ ID NO 4
<211> LENGTH: 170
<212> TYPE: PRT
<213> ORGANISM: Homo sapiens -continued

```
<400> SEQUENCE: 4

Met Arg Ala Leu Glu Gly Pro Gly Leu Ser Leu Leu Cys Leu Val Leu
  1               5                  10                  15

Ala Leu Pro Ala Leu Leu Pro Val Pro Ala Val Arg Gly Val Ala Glu
             20                  25                  30

Thr Pro Thr Tyr Pro Trp Arg Asp Ala Glu Thr Gly Glu Arg Leu Val
         35                  40                  45

Cys Ala Gln Cys Pro Pro Gly Thr Phe Val Gln Arg Pro Cys Arg Arg
     50                  55                  60

Asp Ser Pro Thr Thr Cys Gly Pro Cys Pro Arg His Tyr Thr Gln
 65                  70                  75                  80

Phe Trp Asn Tyr Leu Glu Arg Cys Arg Tyr Cys Asn Val Leu Cys Gly
                 85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
        115                 120                 125

His Ala Ser Cys Pro Pro Gly Ala Gly Val Ile Ala Pro Gly Glu Ser
130                 135                 140

Trp Ala Arg Gly Gly Ala Pro Arg Ser Gly Gly Arg Arg Cys Gly Arg
145                 150                 155                 160

Gly Gln Val Ala Gly Pro Ser Leu Ala Pro
                165                 170

<210> SEQ ID NO 5
<211> LENGTH: 455
<212> TYPE: PRT
<213> ORGANISM: Homo sapiens

<400> SEQUENCE: 5

Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
             20                  25                  30

His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
```

```
                    195                 200                 205
Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
                260                 265                 270

Phe Ser Pro Thr Pro Gly Phe Thr Pro Thr Leu Gly Phe Ser Pro Val
                275                 280                 285

Pro Ser Ser Thr Phe Thr Ser Ser Thr Tyr Thr Pro Gly Asp Cys
                290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
                355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
                435                 440                 445

Pro Ala Pro Ser Leu Leu Arg
450                 455

<210> SEQ ID NO 6
<211> LENGTH: 461
<212> TYPE: PRT
<213> ORGANISM: Homo sapiens

<400> SEQUENCE: 6

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
                35                  40                  45

Thr Ala Gln Met Cys Cys Ser Lys Cys Ser Pro Gly Gln His Ala Lys
                50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
                100                 105                 110

Glu Gln Asn Arg Ile Cys Thr Cys Arg Pro Gly Trp Tyr Cys Ala Leu
```

```
            115                 120                 125
Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
                260                 265                 270

Leu Leu Ile Ile Gly Val Val Asn Cys Val Ile Met Thr Gln Val Lys
            275                 280                 285

Lys Lys Pro Leu Cys Leu Gln Arg Glu Ala Lys Val Pro His Leu Pro
        290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
        355                 360                 365

Asp Ser Ser Pro Gly Gly His Gly Thr Gln Val Asn Val Thr Cys Ile
    370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
        435                 440                 445

Leu Pro Leu Gly Val Pro Asp Ala Gly Met Lys Pro Ser
    450                 455                 460

<210> SEQ ID NO 7
<211> LENGTH: 427
<212> TYPE: PRT
<213> ORGANISM: Homo sapiens

<400> SEQUENCE: 7

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
```

```
                35                 40                  45
Leu Gly Glu Gly Val Ala Gln Pro Cys Gly Ala Asn Gln Thr Val Cys
             50                  55                  60
Glu Pro Cys Leu Asp Ser Val Thr Phe Ser Asp Val Val Ser Ala Thr
 65                  70                  75                  80
Glu Pro Cys Lys Pro Cys Thr Glu Cys Val Gly Leu Gln Ser Met Ser
             85                  90                  95
Ala Pro Cys Val Glu Ala Asp Asp Ala Val Cys Arg Cys Ala Tyr Gly
            100                 105                 110
Tyr Tyr Gln Asp Glu Thr Thr Gly Arg Cys Glu Ala Cys Arg Val Cys
            115                 120                 125
Glu Ala Gly Ser Gly Leu Val Phe Ser Cys Gln Asp Lys Gln Asn Thr
            130                 135                 140
Val Cys Glu Glu Cys Pro Asp Gly Thr Tyr Ser Asp Glu Ala Asn His
145                 150                 155                 160
Val Asp Pro Cys Leu Pro Cys Thr Val Cys Glu Asp Thr Glu Arg Gln
                165                 170                 175
Leu Arg Glu Cys Thr Arg Trp Ala Asp Ala Glu Cys Glu Glu Ile Pro
                180                 185                 190
Gly Arg Trp Ile Thr Arg Ser Thr Pro Pro Glu Gly Ser Asp Ser Thr
                195                 200                 205
Ala Pro Ser Thr Gln Glu Pro Glu Ala Pro Pro Glu Gln Asp Leu Ile
            210                 215                 220
Ala Ser Thr Val Ala Gly Val Val Thr Thr Val Met Gly Ser Ser Gln
225                 230                 235                 240
Pro Val Val Thr Arg Gly Thr Thr Asp Asn Leu Ile Pro Val Tyr Cys
                245                 250                 255
Ser Ile Leu Ala Ala Val Val Val Gly Leu Val Ala Tyr Ile Ala Phe
            260                 265                 270
Lys Arg Trp Asn Ser Cys Lys Gln Asn Lys Gln Gly Ala Asn Ser Arg
            275                 280                 285
Pro Val Asn Gln Thr Pro Pro Pro Glu Gly Glu Lys Leu His Ser Asp
            290                 295                 300
Ser Gly Ile Ser Val Asp Ser Gln Ser Leu His Asp Gln Gln Pro His
305                 310                 315                 320
Thr Gln Thr Ala Ser Gly Gln Ala Leu Lys Gly Asp Gly Gly Leu Tyr
                325                 330                 335
Ser Ser Leu Pro Pro Ala Lys Arg Glu Glu Val Glu Lys Leu Leu Asn
                340                 345                 350
Gly Ser Ala Gly Asp Thr Trp Arg His Leu Ala Gly Glu Leu Gly Tyr
            355                 360                 365
Gln Pro Glu His Ile Asp Ser Phe Thr His Glu Ala Cys Pro Val Arg
            370                 375                 380
Ala Leu Leu Ala Ser Trp Ala Thr Gln Asp Ser Ala Thr Leu Asp Ala
385                 390                 395                 400
Leu Leu Ala Ala Leu Arg Arg Ile Gln Arg Ala Asp Leu Val Glu Ser
                405                 410                 415
Leu Cys Ser Glu Ser Thr Ala Thr Ser Pro Val
            420                 425

<210> SEQ ID NO 8
<211> LENGTH: 415
<212> TYPE: PRT
<213> ORGANISM: Homo sapiens
```

<400> SEQUENCE: 8

```
Met Arg Leu Pro Arg Ala Ser Ser Pro Cys Gly Leu Ala Trp Gly Pro
 1               5                  10                  15
Leu Leu Leu Gly Leu Ser Gly Leu Leu Val Ala Ser Gln Pro Gln Leu
             20                  25                  30
Val Pro Pro Tyr Arg Ile Glu Asn Gln Thr Cys Trp Asp Gln Asp Lys
         35                  40                  45
Glu Tyr Tyr Glu Pro Met His Asp Val Cys Cys Ser Arg Cys Pro Pro
     50                  55                  60
Gly Glu Phe Val Phe Ala Val Cys Ser Arg Ser Gln Asp Thr Val Cys
 65                  70                  75                  80
Lys Thr Cys Pro His Asn Ser Tyr Asn Glu His Trp Asn His Leu Ser
                 85                  90                  95
Thr Cys Gln Leu Cys Arg Pro Cys Asp Ile Val Leu Gly Phe Glu Glu
            100                 105                 110
Val Ala Pro Cys Thr Ser Asp Arg Lys Ala Glu Cys Arg Cys Gln Pro
        115                 120                 125
Gly Met Ser Cys Val Tyr Leu Asp Asn Glu Cys Val His Cys Glu Glu
130                 135                 140
Glu Arg Leu Val Leu Cys Gln Pro Gly Thr Glu Ala Glu Val Thr Asp
145                 150                 155                 160
Glu Ile Met Asp Thr Asp Val Asn Cys Val Pro Cys Lys Pro Gly His
                165                 170                 175
Phe Gln Asn Thr Ser Ser Pro Arg Ala Arg Cys Gln Pro His Thr Arg
            180                 185                 190
Cys Glu Ile Gln Gly Leu Val Glu Ala Ala Pro Gly Thr Ser Tyr Ser
        195                 200                 205
Asp Thr Ile Cys Lys Asn Pro Pro Glu Pro Gly Ala Met Leu Leu Leu
210                 215                 220
Ala Ile Leu Leu Ser Leu Val Leu Phe Leu Leu Phe Thr Thr Val Leu
225                 230                 235                 240
Ala Cys Ala Trp Met Arg His Pro Ser Leu Cys Arg Lys Leu Gly Thr
                245                 250                 255
Leu Leu Lys Arg His Pro Glu Gly Glu Glu Ser Pro Pro Cys Pro Ala
            260                 265                 270
Pro Arg Ala Asp Pro His Phe Pro Asp Leu Ala Glu Pro Leu Leu Pro
        275                 280                 285
Met Ser Gly Asp Leu Ser Pro Ser Pro Ala Gly Pro Pro Thr Ala Pro
290                 295                 300
Ser Leu Glu Glu Val Val Leu Gln Gln Gln Ser Pro Leu Val Gln Ala
305                 310                 315                 320
Arg Glu Leu Glu Ala Glu Pro Gly Glu His Gly Gln Val Ala His Gly
                325                 330                 335
Ala Asn Gly Ile His Val Thr Gly Gly Ser Val Thr Val Thr Gly Asn
            340                 345                 350
Ile Tyr Ile Tyr Asn Gly Pro Val Leu Gly Gly Thr Arg Gly Pro Gly
        355                 360                 365
Asp Pro Pro Ala Pro Pro Glu Pro Pro Tyr Pro Thr Pro Glu Glu Gly
370                 375                 380
Ala Pro Gly Pro Ser Glu Leu Ser Thr Pro Tyr Gln Glu Asp Gly Lys
385                 390                 395                 400
Ala Trp His Leu Ala Glu Thr Glu Thr Leu Gly Cys Gln Asp Leu
                405                 410                 415
```

<210> SEQ ID NO 9
<211> LENGTH: 335
<212> TYPE: PRT
<213> ORGANISM: Homo sapiens

<400> SEQUENCE: 9

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 10
<211> LENGTH: 260
<212> TYPE: PRT
<213> ORGANISM: Homo sapiens

<400> SEQUENCE: 10

Met Ala Arg Pro His Pro Trp Trp Leu Cys Val Leu Gly Thr Leu Val

```
                1               5                  10                 15
Gly Leu Ser Ala Thr Pro Ala Pro Lys Ser Cys Pro Glu Arg His Tyr
                        20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His Thr Arg Pro His
65                  70                  75                  80

Cys Glu Ser Cys Arg His Cys Asn Ser Gly Leu Leu Val Arg Asn Cys
                        85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                        165                 170                 175

His Trp Pro Pro Gln Arg Ser Leu Cys Ser Ser Asp Phe Ile Arg Ile
                180                 185                 190

Leu Val Ile Phe Ser Gly Met Phe Leu Val Phe Thr Leu Ala Gly Ala
            195                 200                 205

Leu Phe Leu His Gln Arg Arg Lys Tyr Arg Ser Asn Lys Gly Glu Ser
        210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                        245                 250                 255

Ala Cys Ser Pro
                260

<210> SEQ ID NO 11
<211> LENGTH: 595
<212> TYPE: PRT
<213> ORGANISM: Homo sapiens

<400> SEQUENCE: 11

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                        85                  90                  95

Pro Cys Ala Trp Asn Ser Ser Arg Val Cys Glu Cys Arg Pro Gly Met
                100                 105                 110

Phe Cys Ser Thr Ser Ala Val Asn Ser Cys Ala Arg Cys Phe Phe His
```

```
                115                 120                 125
Ser Val Cys Pro Ala Gly Met Ile Val Lys Phe Pro Gly Thr Ala Gln
130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
                180                 185                 190

Pro Val Arg Gly Gly Thr Arg Leu Ala Gln Glu Ala Ala Ser Lys Leu
                195                 200                 205

Thr Arg Ala Pro Asp Ser Pro Ser Ser Val Gly Arg Pro Ser Ser Asp
210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
                260                 265                 270

Cys Ala Trp Asn Ser Ser Arg Thr Cys Glu Cys Arg Pro Gly Met Ile
                275                 280                 285

Cys Ala Thr Ser Ala Thr Asn Ser Cys Ala Arg Cys Val Pro Tyr Pro
                290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
                340                 345                 350

Ser Leu Leu Val Asp Ser Gln Ala Ser Lys Thr Leu Pro Ile Pro Thr
                355                 360                 365

Ser Ala Pro Val Ala Leu Ser Ser Thr Gly Lys Pro Val Leu Asp Ala
370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
                420                 425                 430

Leu Glu Leu Val Asp Ser Arg Pro Arg Arg Ser Ser Thr Gln Leu Arg
                435                 440                 445

Ser Gly Ala Ser Val Thr Glu Pro Val Ala Glu Glu Arg Gly Leu Met
450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
                500                 505                 510

Lys Ile Glu Lys Ile Tyr Ile Met Lys Ala Asp Thr Val Ile Val Gly
                515                 520                 525

Thr Val Lys Ala Glu Leu Pro Glu Gly Arg Gly Leu Ala Gly Pro Ala
530                 535                 540
```

Glu Pro Glu Leu Glu Glu Leu Glu Ala Asp His Thr Pro His Tyr
545                 550                 555                 560

Pro Glu Gln Glu Thr Glu Pro Leu Gly Ser Cys Ser Asp Val Met
            565                 570                 575

Leu Ser Val Glu Glu Gly Lys Glu Asp Pro Leu Pro Thr Ala Ala
        580                 585                 590

Ser Gly Lys
        595

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275

<210> SEQ ID NO 13
<211> LENGTH: 255
<212> TYPE: PRT
<213> ORGANISM: Homo sapiens -continued

```
<400> SEQUENCE: 13

Met Gly Asn Ser Cys Tyr Asn Ile Val Ala Thr Leu Leu Val Leu
 1               5                  10                  15

Asn Phe Glu Arg Thr Arg Ser Leu Gln Asp Pro Cys Ser Asn Cys
                20                  25                  30

Pro Ala Gly Thr Phe Cys Asp Asn Asn Arg Asn Gln Ile Cys Ser
                35                  40                  45

Pro Cys Pro Pro Asn Ser Phe Ser Ser Ala Gly Gly Gln Arg Thr
                50                  55                  60

Cys Asp Ile Cys Arg Gln Cys Lys Gly Val Phe Arg Thr Arg Lys
 65                  70                  75                  80

Glu Cys Ser Ser Thr Ser Asn Ala Glu Cys Asp Cys Thr Pro Gly
                85                  90                  95

Phe His Cys Leu Gly Ala Gly Cys Ser Met Cys Glu Gln Asp Cys
                100                 105                 110

Lys Gln Gly Gln Glu Leu Thr Lys Lys Gly Cys Lys Asp Cys Cys
                115                 120                 125

Phe Gly Thr Phe Asn Asp Gln Lys Arg Gly Ile Cys Arg Pro Trp
130                 135                 140

Thr Asn Cys Ser Leu Asp Gly Lys Ser Val Leu Val Asn Gly Thr
145                 150                 155                 160

Lys Glu Arg Asp Val Val Cys Gly Pro Ser Pro Ala Asp Leu Ser
                165                 170                 175

Pro Gly Ala Ser Ser Val Thr Pro Pro Ala Pro Ala Arg Glu Pro
                180                 185                 190

Gly His Ser Pro Gln Ile Ile Ser Phe Phe Leu Ala Leu Thr Ser
                195                 200                 205

Thr Ala Leu Leu Phe Leu Leu Phe Phe Leu Thr Leu Arg Phe Ser
210                 215                 220

Val Val Lys Arg Gly Arg Lys Lys Leu Leu Tyr Ile Phe Lys Gln
225                 230                 235                 240

Pro Phe Met Arg Pro Val Gln Thr Thr Gln Glu Glu Asp Gly Cys
                245                 250                 255

Ser Cys Arg Phe Pro Glu Glu Glu Glu Gly Gly Cys Glu Leu
                245                 250                 255

<210> SEQ ID NO 14
<211> LENGTH: 277
<212> TYPE: PRT
<213> ORGANISM: Homo sapiens

<400> SEQUENCE: 14

Met Cys Val Gly Ala Arg Arg Leu Gly Arg Gly Pro Cys Ala Ala
 1               5                  10                  15

Leu Leu Leu Leu Gly Leu Gly Leu Ser Thr Val Thr Gly Leu His
                20                  25                  30

Cys Val Gly Asp Thr Tyr Pro Ser Asn Asp Arg Cys Cys His Glu
                35                  40                  45

Cys Arg Pro Gly Asn Gly Met Val Ser Arg Cys Ser Arg Ser Gln
                50                  55                  60

Asn Thr Val Cys Arg Pro Cys Gly Pro Gly Phe Tyr Asn Asp Val
 65                  70                  75                  80

Val Ser Ser Lys Pro Cys Lys Pro Cys Thr Trp Cys Asn Leu Arg
                85                  90                  95

Ser Gly Ser Glu Arg Lys Gln Leu Cys Thr Ala Thr Gln Asp Thr
                100                 105                 110

Val Cys Arg Cys Arg Ala Gly Thr Gln Pro Leu Asp Ser Tyr Lys

Pro Gly Val Asp Cys Ala Pro Cys
```

```
            115                 120                 125
Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 15
<211> LENGTH: 349
<212> TYPE: PRT
<213> ORGANISM: Homo sapiens

<400> SEQUENCE: 15

Met Lys Ser Val Leu Tyr Leu Tyr Ile Leu Phe Leu Ser Cys Ile Ile
1               5                   10                  15

Ile Asn Gly Arg Asp Ala Ala Pro Tyr Thr Pro Pro Asn Gly Lys Cys
            20                  25                  30

Lys Asp Thr Glu Tyr Lys Arg His Asn Leu Cys Cys Leu Ser Cys Pro
        35                  40                  45

Pro Gly Thr Tyr Ala Ser Arg Leu Cys Asp Ser Lys Thr Asn Thr Gln
    50                  55                  60

Cys Thr Pro Cys Gly Ser Gly Thr Phe Thr Ser Arg Asn Asn His Leu
65                  70                  75                  80

Pro Ala Cys Leu Ser Cys Asn Gly Arg Cys Asn Ser Asn Gln Val Glu
                85                  90                  95

Thr Arg Ser Cys Asn Thr Thr His Asn Arg Ile Cys Glu Cys Ser Pro
            100                 105                 110

Gly Tyr Tyr Cys Leu Leu Lys Gly Ser Ser Gly Cys Lys Ala Cys Val
        115                 120                 125

Ser Gln Thr Lys Cys Gly Ile Gly Tyr Gly Val Ser Gly His Thr Ser
    130                 135                 140

Val Gly Asp Val Ile Cys Ser Pro Cys Gly Phe Gly Thr Tyr Ser His
145                 150                 155                 160

Thr Val Ser Ser Ala Asp Lys Cys Glu Pro Val Pro Asn Asn Thr Phe
                165                 170                 175

Asn Tyr Ile Asp Val Glu Ile Thr Leu Tyr Pro Val Asn Asp Thr Ser
            180                 185                 190

Cys Thr Arg Thr Thr Thr Thr Gly Leu Ser Glu Ser Ile Leu Thr Ser
        195                 200                 205

Glu Leu Thr Ile Thr Met Asn His Thr Asp Cys Asn Pro Val Phe Arg
```

```
                    210                 215                 220
Glu Glu Tyr Phe Ser Val Leu Asn Lys Val Ala Thr Ser Gly Phe Phe
225                 230                 235                 240

Thr Gly Glu Asn Arg Tyr Gln Asn Ile Ser Lys Val Cys Thr Leu Asn
                245                 250                 255

Phe Glu Ile Lys Cys Asn Asn Lys Gly Ser Ser Phe Lys Gln Leu Thr
            260                 265                 270

Lys Ala Lys Asn Asp Asp Gly Met Met Ser His Ser Glu Thr Val Thr
        275                 280                 285

Leu Ala Gly Asp Cys Leu Ser Ser Val Asp Ile Tyr Ile Leu Tyr Ser
290                 295                 300

Asn Thr Asn Ala Gln Asp Tyr Glu Thr Asp Thr Ile Ser Tyr Arg Val
305                 310                 315                 320

Gly Asn Val Leu Asp Asp Ser His Met Pro Gly Ser Cys Asn Ile
                325                 330                 335

His Lys Pro Ile Thr Asn Ser Lys Pro Thr Arg Phe Leu
                340                 345

<210> SEQ ID NO 16
<211> LENGTH: 355
<212> TYPE: PRT
<213> ORGANISM: Homo sapiens

<400> SEQUENCE: 16

Met Lys Ser Tyr Ile Leu Leu Leu Leu Ser Cys Ile Ile Ile
1               5                   10                  15

Asn Ser Asp Ile Thr Pro His Glu Pro Ser Asn Gly Lys Cys Lys Asp
                20                  25                  30

Asn Glu Tyr Lys Arg His His Leu Cys Cys Leu Ser Cys Pro Pro Gly
            35                  40                  45

Thr Tyr Ala Ser Arg Leu Cys Asp Ser Lys Thr Asn Thr Asn Thr Gln
        50                  55                  60

Cys Thr Pro Cys Ala Ser Asp Thr Phe Thr Ser Arg Asn Asn His Leu
65                  70                  75                  80

Pro Ala Cys Leu Ser Cys Asn Gly Arg Cys Asp Ser Asn Gln Val Glu
                85                  90                  95

Thr Arg Ser Cys Asn Thr Thr His Asn Arg Ile Cys Asp Cys Ala Pro
            100                 105                 110

Gly Tyr Tyr Cys Phe Leu Lys Gly Ser Ser Gly Cys Lys Ala Cys Val
        115                 120                 125

Ser Gln Thr Lys Cys Gly Ile Gly Tyr Gly Val Ser Gly His Thr Pro
130                 135                 140

Thr Gly Asp Val Val Cys Ser Pro Cys Gly Leu Gly Thr Tyr Ser His
145                 150                 155                 160

Thr Val Ser Ser Val Asp Lys Cys Glu Pro Val Pro Ser Asn Thr Phe
                165                 170                 175

Asn Tyr Ile Asp Val Glu Ile Asn Leu Tyr Pro Val Asn Asp Thr Ser
            180                 185                 190

Cys Thr Arg Thr Thr Thr Thr Gly Leu Ser Glu Ser Ile Ser Thr Ser
        195                 200                 205

Glu Leu Thr Ile Thr Met Asn His Lys Asp Cys Asp Pro Val Phe Arg
210                 215                 220

Asn Gly Tyr Phe Ser Val Leu Asn Glu Val Ala Thr Ser Gly Phe Phe
225                 230                 235                 240

Thr Gly Gln Asn Arg Tyr Gln Asn Ile Ser Lys Val Cys Thr Leu Asn
```

```
                    245                 250                 255
Phe Glu Ile Lys Cys Asn Asn Lys Asp Ser Tyr Ser Ser Ser Lys Gln
                260                 265                 270

Leu Thr Lys Thr Lys Asn Asp Asp Ser Ile Met Pro His Ser Glu
            275                 280                 285

Ser Val Thr Leu Val Gly Asp Cys Leu Ser Val Asp Ile Tyr Ile
    290                 295                 300

Leu Tyr Ser Asn Thr Asn Thr Gln Asp Tyr Glu Thr Asp Thr Ile Ser
305                 310                 315                 320

Tyr His Val Gly Asn Val Leu Asp Val Asp Ser His Met Pro Gly Arg
                325                 330                 335

Cys Asp Thr His Lys Leu Ile Thr Asn Ser Asn Ser Gln Tyr Pro Thr
            340                 345                 350

His Phe Leu
        355

<210> SEQ ID NO 17
<211> LENGTH: 499
<212> TYPE: DNA
<213> ORGANISM: Homo sapiens
<220> FEATURE:
<221> NAME/KEY: misc_feature
<222> LOCATION: (20)
<223> OTHER INFORMATION: n equals a, t, g, or c
<221> NAME/KEY: misc_feature
<222> LOCATION: (41)
<223> OTHER INFORMATION: n equals a, t, g, or c
<221> NAME/KEY: misc_feature
<222> LOCATION: (160)..(161)
<223> OTHER INFORMATION: n equals a, t, g, or c
<221> NAME/KEY: misc_feature
<222> LOCATION: (164)
<223> OTHER INFORMATION: n equals a, t, g, or c
<221> NAME/KEY: misc_feature
<222> LOCATION: (181)
<223> OTHER INFORMATION: n equals a, t, g, or c
<221> NAME/KEY: misc_feature
<222> LOCATION: (205)
<223> OTHER INFORMATION: n equals a, t, g, or c
<221> NAME/KEY: misc_feature
<222> LOCATION: (207)
<223> OTHER INFORMATION: n equals a, t, g, or c
<221> NAME/KEY: misc_feature
<222> LOCATION: (212)
<223> OTHER INFORMATION: n equals a, t, g, or c
<221> NAME/KEY: misc_feature
<222> LOCATION: (231)
<223> OTHER INFORMATION: n equals a, t, g, or c
<221> NAME/KEY: misc_feature
<222> LOCATION: (248)
<223> OTHER INFORMATION: n equals a, t, g, or c
<221> NAME/KEY: misc_feature
<222> LOCATION: (277)
<223> OTHER INFORMATION: n equals a, t, g, or c
<221> NAME/KEY: misc_feature
<222> LOCATION: (322)
<223> OTHER INFORMATION: n equals a, t, g, or c
<221> NAME/KEY: misc_feature
<222> LOCATION: (330)
<223> OTHER INFORMATION: n equals a, t, g, or c
<221> NAME/KEY: misc_feature
<222> LOCATION: (353)
<223> OTHER INFORMATION: n equals a, t, g, or c
<221> NAME/KEY: misc_feature
<222> LOCATION: (372)
<223> OTHER INFORMATION: n equals a, t, g, or c
<221> NAME/KEY: misc_feature
<222> LOCATION: (378)
<223> OTHER INFORMATION: n equals a, t, g, or c
<221> NAME/KEY: misc_feature
<222> LOCATION: (391)
<223> OTHER INFORMATION: n equals a, t, g, or c
```

<221> NAME/KEY: misc_feature
<222> LOCATION: (394)
<223> OTHER INFORMATION: n equals a, t, g, or c
<221> NAME/KEY: misc_feature
<222> LOCATION: (402)
<223> OTHER INFORMATION: n equals a, t, g, or c
<221> NAME/KEY: misc_feature
<222> LOCATION: (407)
<223> OTHER INFORMATION: n equals a, t, g, or c
<221> NAME/KEY: misc_feature
<222> LOCATION: (421)
<223> OTHER INFORMATION: n equals a, t, g, or c
<221> NAME/KEY: misc_feature
<222> LOCATION: (421)
<223> OTHER INFORMATION: n equals a, t, g, or c
<221> NAME/KEY: misc_feature
<222> LOCATION: (437)..(438)
<223> OTHER INFORMATION: n equals a, t, g, or c
<221> NAME/KEY: misc_feature
<222> LOCATION: (446)
<223> OTHER INFORMATION: n equals a, t, g, or c
<221> NAME/KEY: misc_feature
<222> LOCATION: (460)
<223> OTHER INFORMATION: n equals a, t, g, or c
<221> NAME/KEY: misc_feature
<222> LOCATION: (466)
<223> OTHER INFORMATION: n equals a, t, g, or c
<221> NAME/KEY: misc_feature
<222> LOCATION: (474)
<223> OTHER INFORMATION: n equals a, t, g, or c
<221> NAME/KEY: misc_feature
<222> LOCATION: (482)..(484)
<223> OTHER INFORMATION: n equals a, t, g, or c
<221> NAME/KEY: misc_feature
<222> LOCATION: (486)
<223> OTHER INFORMATION: n equals a, t, g, or c
<221> NAME/KEY: misc_feature
<222> LOCATION: (496)
<223> OTHER INFORMATION: n equals a, t, g, or c

<400> SEQUENCE: 17

```
ggcacgagca gggtcctgtn tccgccctga gccgcgctct ncctgctcca gcaaggacca      60
tgagggcgct ggaggggcca ggcctgtcgc tgctgtgcct ggtgttggcg ctgcctgccc     120
tgctgccggt gccggctgta cgcggagtgg cagaaacacn nacntacccc tggcgggacg     180
nagagacagg ggagcggctg gtgtntnccc antgccccc aggcacctttt ntgcagcggc     240 cgtgccgncg agacagcccc acgacgtgtg gcccgtntcc accgcgccac tacacgcatt     300
ctggaactac ctggagcgct gncgttactn caacgtcctc tgcggggagc gtnaggagga     360
ggcacgggtt tnccacgnca accacaaccg nggnttaccg tngccgnacc ggtttcttcg     420
nggcaagttg gtttttnntt tggagnaagg attcgtgttn caattnattg acgnagtgat     480
tnnncncggg aaactnaaa                                                  499
```

<210> SEQ ID NO 18
<211> LENGTH: 191
<212> TYPE: DNA
<213> ORGANISM: Homo sapiens
<220> FEATURE:
<221> NAME/KEY: misc_feature
<222> LOCATION: (42)
<223> OTHER INFORMATION: n equals a, t, g, or c
<221> NAME/KEY: misc_feature
<222> LOCATION: (106)
<223> OTHER INFORMATION: n equals a, t, g, or c
<221> NAME/KEY: misc_feature
<222> LOCATION: (125)
<223> OTHER INFORMATION: n equals a, t, g, or c
<221> NAME/KEY: misc_feature
<222> LOCATION: (188)
<223> OTHER INFORMATION: n equals a, t, g, or c

<400> SEQUENCE: 18

```
cgcaactgca cggccctggg actggccctc aatgtgccag gntcttcctc ccatgacacc        60
ctgtgcacca gctgcactgg cttccccctc agcaccaggg taccangagc tgaggagtgt       120
gagcntgccg tcatcgactt tttggctttc caggacatct ccatcaagag gctgcagcgg       180
ctgctcangc c                                                           191

<210> SEQ ID NO 19
<211> LENGTH: 26
<212> TYPE: DNA
<213> ORGANISM: Homo sapiens

<400> SEQUENCE: 19
cgcccatggc agaaacaccc acctac                                            26

<210> SEQ ID NO 20
<211> LENGTH: 26
<212> TYPE: DNA
<213> ORGANISM: Homo sapiens

<400> SEQUENCE: 20
cgcaagcttc tctttcagtg caagtg                                            26

<210> SEQ ID NO 21
<211> LENGTH: 28
<212> TYPE: DNA
<213> ORGANISM: Homo sapiens

<400> SEQUENCE: 21
cgcaagcttc tcctcagctc ctgcagtg                                          28

<210> SEQ ID NO 22
<211> LENGTH: 36
<212> TYPE: DNA
<213> ORGANISM: Homo sapiens

<400> SEQUENCE: 22
cgcggatccg ccatcatgag ggcgtggagg ggccag                                 36

<210> SEQ ID NO 23
<211> LENGTH: 26
<212> TYPE: DNA
<213> ORGANISM: Homo sapiens

<400> SEQUENCE: 23
cgcggtaccc tctttcagtg caagtg                                            26

<210> SEQ ID NO 24
<211> LENGTH: 28
<212> TYPE: DNA
<213> ORGANISM: Homo sapiens

<400> SEQUENCE: 24
cgcggtaccc tcctcagctc ctgcagtg                                          28
```